United States Patent
Bleiel

(10) Patent No.: US 10,898,442 B2
(45) Date of Patent: Jan. 26, 2021

(54) MICROENCAPSULATES CONTAINING STABILISED LIPID, AND METHODS FOR THE PRODUCTION THEREOF

(71) Applicant: Anabio Technologies Limited, Dublin (IE)

(72) Inventor: Sinead Bleiel, Dublin (IE)

(73) Assignee: Anabio Technologies Limited, Dublin (IE)

( * ) Notice: Subject to any disclaimer, the term of this patent is extended or adjusted under 35 U.S.C. 154(b) by 0 days.

(21) Appl. No.: 15/564,635

(22) PCT Filed: Jun. 2, 2016

(86) PCT No.: PCT/EP2016/062500
§ 371 (c)(1),
(2) Date: Oct. 5, 2017

(87) PCT Pub. No.: WO2016/193373
PCT Pub. Date: Dec. 8, 2016

(65) Prior Publication Data
US 2018/0071224 A1 Mar. 15, 2018

(30) Foreign Application Priority Data
Jun. 3, 2015 (GB) .................................. 1509606.8

(51) Int. Cl.
| | | |
|---|---|---|
| *A61K 9/51* | (2006.01) | |
| *A61K 9/50* | (2006.01) | |
| *A23P 10/35* | (2016.01) | |
| *A23P 30/25* | (2016.01) | |
| *A23L 27/00* | (2016.01) | |
| *A23L 29/275* | (2016.01) | |
| *A23L 33/12* | (2016.01) | |
| *A23P 10/30* | (2016.01) | |
| *A23L 33/115* | (2016.01) | |
| *A61K 9/107* | (2006.01) | |
| *A61K 35/612* | (2015.01) | |
| *A61K 47/44* | (2017.01) | |

(52) U.S. Cl.
CPC ............ *A61K 9/5036* (2013.01); *A23L 27/72* (2016.08); *A23L 29/275* (2016.08); *A23L 33/115* (2016.08); *A23L 33/12* (2016.08); *A23P 10/30* (2016.08); *A23P 10/35* (2016.08); *A23P 30/25* (2016.08); *A61K 9/1075* (2013.01); *A61K 35/612* (2013.01); *A61K 47/44* (2013.01); *A23V 2002/00* (2013.01); *A23V 2250/1862* (2013.01); *A23V 2250/1868* (2013.01); *A23V 2250/511* (2013.01); *A23V 2250/5114* (2013.01); *A23V 2250/616* (2013.01); *A23V 2250/628* (2013.01)

(58) Field of Classification Search
None
See application file for complete search history.

(56) References Cited

U.S. PATENT DOCUMENTS

| | | | |
|---|---|---|---|
| 2008/0113031 A1* | 5/2008 | Moodley | A61K 9/5073 424/490 |
| 2010/0055281 A1* | 3/2010 | Barrow | A23D 7/0053 426/546 |
| 2010/0322995 A1 | 12/2010 | Geselle | |

FOREIGN PATENT DOCUMENTS

| | | |
|---|---|---|
| EP | 2111854 A1 | 10/2009 |
| WO | WO-2008/012329 A2 | 1/2008 |
| WO | WO-2009/029406 A1 | 3/2009 |

* cited by examiner

*Primary Examiner* — Susan T Tran
(74) *Attorney, Agent, or Firm* — Cesari and McKenna, LLP

(57) ABSTRACT

The invention provides a gelated mono-nuclear microencapsulate comprising a lipid emulsion core encapsulated within a gastro-resistant, ileal sensitive, polymerized chitosan membrane shell, wherein the lipid emulsion core comprises denatured or hydrolysed protein and carbohydrate. In one embodiment of the invention, the emulsion is a microemulsion, and typically comprises a surfactant and a co-surfactant or at least two carbohydrates, for example sucrose and a maltodextrin. In one embodiment of the invention, the lipid is a marine derived lipid such as fish oil, krill oil, or nutraceutical fatty acids. In other embodiment, the lipid is a fatty acid such as DHA or ARA, or a lipid derived from seeds, nuts or eggs.

16 Claims, 12 Drawing Sheets

|  | Krill Oil | Algal Oil | Fish Oil |
|---|---|---|---|
| Triacylglycerol | 40% | 94.0% | 99% |
| Diacylglycerol | 1.2% | 3% | |
| Monoacylglycerol | <1% | <1% | |
| Free fatty acids | 4.2% | <1% | <1% |
| Total neutral lipids | 46.8% | 97% | 99% |
| Phosphatidylcholin | 35% | | |
| Lyso-phosphatidylcholin | 3.1% | | |
| Phosphatidyletanolamin | 2.1% | | |
| Total polar lipids | 40% | | |
| Astaxanthin | >210 ppm | | |

Fig. 1.

| Powder | TG | PL | Particle Size (D, 0.9) microns | Omega -3 (DHA/EPA (g/100g oil) | Surface Fat (g/100g powder) |
|---|---|---|---|---|---|
| A | YES | YES | 2.95 μm | 40 (25: 15) | 23.12 |
| B | YES | - | 0.34 μm | 40 (35:5) | 0.91 |
| C | YES | - | 0.21 μm | 40 (10:30) | 0.24 |
| D | YES | - | 0.19 μm | 40 (16: 24) | 0.08 |

Fig. 2.

MICROENCAPSULATES CONTAINING STABILISED LIPID, AND METHODS FOR THE PRODUCTION THEREOF

CROSS REFERENCE TO RELATED APPLICATIONS

This application is the National Stage of International Application No. PCT/EP2016/062500, filed on Jun. 2, 2016, which claims the benefit of British Application No. 1509606.8, filed on Jun. 3, 2015. The contents of both applications are hereby incorporated by reference in their entirety.

TECHNICAL FIELD

The invention relates to method of producing microcapsules by double extrusion, having a crosslinked hydrocolloid matrix consisting of protein and chitin origin.

BACKGROUND TO THE INVENTION

Dietary intake of the marine omega-3 fatty acids EPA and DHA has been linked to many health benefits, from improved cardiovascular health and cognitive function, to reduced levels of inflammation. Health benefits of long chain polyunsaturated fatty acids (PUFA's) are well-recognized and fully endorsed by the World Health Organization, WHO. However, the direct addition of PUFA's into food products and supplements is a technological challenge due to oxidative stress, rancidity and instability experienced by fatty acids including DHA and ARA, which reduces shelf life of foods & supplements with PUFA's. The same technical challenges apply to hill oil, which is receiving increased attention as a nutritional supplement due to its rich source of PUFA's and it is further claimed to have more rapid absorption relative to triglycerides sourced from fish oils. Encapsulation techniques can inhibit degradation and preserve the quality of products formulated with these compounds. Capsules may also be designed with additional chemical functionality that provides binding sites for cellular recognition, response to changes in pH conditions, or additional protective groups.

Krill are among the most populous animal species on the planet tiny, shrimp-like crustaceans, krill flourish in the frigid waters of the Antarctic Ocean. Because the temperature in that salty environment remains close to the freezing point of fresh water, krill evolved a mechanism to keep their cell membranes fluid. Traditionally, the marine crustacean krill has not been a part of the human diet. In recent times, interest in the organism as a food for human consumption has increased due to a number of factors, including the high nutritional value of the animal, the fact it contains a number of compounds relevant to human health and its relative abundance. In particular, there is significant commercial interest in Krill oil (Tou, Jaczynski, & Chen, 2007) because it is rich in omega-3 polyunsaturated fatty acids (n-3 PUFA) such as eicosapentaenoic (EPA, 20:5n3) and docosahexaenoic (DHA, 22:6n3) acids. These fatty acids are important in reducing the risk of a number of human ailments particularly cardiovascular disease (CVD) (Gigliotti, Davenport, Beamer, Tou, & Jaczynski, 2011). In addition, krill is low (26.1%) in both (short-chain fatty acids) SFAs and (24.2%) monounsaturated (MUFA's) but high (48.5%) in (polyunsaturated fatty acids) PUFAs. Palmitic acid (16:0) is the predominant SFA, oleic acid (18:1 omega-9) is the predominant MUFA, and the PUFA's consist mainly of omega-3 fatty acids. Indeed omega-3 PUFA's account for almost 19% of the total lipid content of krill (Tou et al., 2007). These levels and percentage values of oils may vary on a seasonal basis (Kolakowska, Kolakowski, & Szczygielski, 1994).

Krill oil also contains phospholipids. The phospholipids found in hill oil are the very ones from which our bodies' cell walls are made. Because of this, the beneficial components of hill oil are absorbed more rapidly and easily in comparison to the triacyglycerols which are associated with fish oil products. EPA & DHA bound to these phospholipids are fed into a complex signaling cascade known as the "Eicosanoid system", which regulates a huge array of mammalian body functions. Krill oil contains the antioxidant astaxanthin which can help prevent the formation of damaging free radicals throughout the mammalian body (Lu, Nielsen, Timm-Heinrich, & Jacobsen, 2011). Due to the short life-span (1-2 years), presence at the bottom of the food chain and residence in an unpolluted ecosystem, hill are naturally free of heavy metals and other pollutants (Deutsch, 2007). As a consequence, health-conscious consumers have grown more interested in alternative sources of Omega-3 fatty acids, since fish oil is more likely to contain heavy metals and leave a fishy aftertaste. In recent years, WHO recommend the inclusion of DHA and ARA in specific foods, for example, infant formula (minimum level 40 mg/kg/day ARA and 20 mg/kg/day DHA). To that end, various organizations have established recommended daily intakes for EPA. ARA and DHA ranging from 160 mg (Australia, New Zealand) to >1000 mg (Japan, South Korea). Since typical Western diets fall short of these guidelines, dietary supplementation helps to make up the difference. Commercially, krill oil is supplied almost universally as capsules to be consumed as extra-dietary supplements. Due to its inherent advantages i.e., omega-3 fatty acids bound to phospholipids, naturally stable, pure and sourced sustainably—krill oil has enormous potential in serving the global demand for omega-3 health needs for years to come.

Despite their apparent similarities, there are two important differences between fish oil and krill oil products:

The first point of differentiation is intended benefit and dosage. Fish oil is widely recognized for promoting cardiovascular health and favorably affecting blood lipids. Fish oil taken in sufficient doses lowers triglycerides and favorably modifies other vascular risk factors such as small, dense LDL. Optimal doses for most people of EPA is 1,400 mg and DHA is 1,000 mg. Krill oil also provides EPA and DHA (in the phospholipid forms), but it does not provide them in levels high enough for optimal cardiovascular protection.

The second point of differentiation is the site of action of the two marine oils. Fish oils favorably modulate inflammatory cytokines circulating in the blood, thereby reducing total body inflammation (that's in part how they exert their beneficial cardiovascular effects). Krill oil, on the other hand, has beneficial effects locally in the joint. In one study, krill oil, but not fish oil, reduced infiltration of inflammatory cells into the joint and joint-lining tissues, a vital effect in reducing the pain, swelling, and loss of function in arthritis. In that same study, fish oil, but not krill oil, modulated blood levels of inflammatory cytokines. This study provides a neat picture of the complementary nature of these two marine oils.

International patent application publication No WO 00/23546 discloses methods for extracting lipid fractions from marine and aquatic animal material by acetone extractions. The resulting non-soluble and particulate fraction may be further solvent extracted with ethanol or ethyl acetate to achieve further lipid extractions.

Dietary lipids may undergo auto-, photo-, thermal- and enzymatic oxidation. Auto-oxidation is the most common process and is defined as the spontaneous reaction of atmospheric oxygen with lipids. If auto-oxidation occurs during the shelf-life of a fatty acid product this will significantly compromise the quality of the product and sacrifice consumer acceptance.

In general terms, due to their unsaturated nature, PUFA's are sensitive to oxidation. Both krill and fish oils contain PUFA's such as 5 or 6 double bonds; hence, both fish and hill oils are prone to atmospheric oxidation. Oxidation lowers the nutritional value and quality of fatty foods (van Ruth, Shaker, & Morrissey, 2001). Primary products of lipid oxidation are hydroperoxides which are odourless and flavourless transitionary intermediates. Hydroperoxides decompose to secondary oxidation products, small volatile mechanisms that cause off-aromas associated with oxidative rancidity, pronounced taste and smell of fish and shellfish oils. (Chaiyasit, Elias, McClements, & Decker, 2007). The "fishy odour/flavor" of marine oil is one of the most important problems in the preparation of nutraceuticals for oral consumption. The odour can be extremely stubborn and may remain after trans-esterification. This odour is due to a large number of volatile matter as well as compounds which are formed by oxidative degradation of highly unsaturated fatty acids. These are predominantly unsaturated carbonyl compounds, which can have an intense odor even at very low concentrations. Even if the problem of oral contact is avoided, the problem still remains intact after ingestion where the unpleasant re-gurgitation and breathing with the undesirable odour can be a real problem.

Unsaturated fatty acids (such as DHA and ARA) are generally the reactants affected by such reactions. Oxidation mechanisms in hill oil are more complex than in fish oil as the lipids can degrade to form Strecker aldehydes and pyrroles. Therefore, the traditional methods for measuring oxidation are not suitable for quality control of krill oils (Jacobsen, Torstensen, & Undeland, 2013). For this reason, hill oil must be rapidly extracted (usually solvent extraction or press methods) to prevent oxidation. Once the oil is extracted, the risk of oxidation is lowered, which is further endorsed by the presence of astaxanthin and other antioxidants in the product (Lu et al., 2011).

Autolysis for the purpose of preserving the krill proteins in order to increase the yield of krill meal preparation is also responsible for the unpleasant odour and taste of krill and/or marine extracts caused by a rapid oxidation and hydrolysis of the krill lipids forming a high amount of free fatty acids, lyso-phospholipids and volatile compounds which in turn reduce the stability of krill extracts. Various extraction/deodorization methods developed for fish oil have been tested on krill oil, but none of them reported to be promising. Some methods remove specific components from the oil that would need to be artificially added back after the process. Alternative methods clearly changed the nature of the oil, changing the color of the oil from orange/red to black, with a burnt smell.

More specifically, the smell of frozen krill is caused by dimethyl-sulfide (DMS) and volatile amines. Frozen krill contains 50-3700 ng/g of DMS, more in the cephalothorax than in telson. DMS evokes a flavor specific to crustaceans when its concentration is below about 100 ng/g. The aroma becomes unpleasant when it exceeds the concentration of 1 µg/g, and it becomes offensive when it exceeds several µg/g. Storage at −30° C. is desirable to prevent formation of DMS.

A recent report by Commonwealth Scientific and Industrial Research Organisation (CSIRO) describes the production of a spray-dried powder containing hill oil in a protein/carbohydrate matrix. The authors concluded that stability was improved with regard to heat treatment and extrusion. Although reports indicate that krill oil may be more stable than other fish oil products, the presence of off-flavors remain an issue due to the presence of the PUFA's. This is an imperative issue with these products due to the fact that even minute amounts of oxidation products are detectable to the human palate (Kris-Etherton, Harris, & Appel, 2003). Effective micro-encapsulation of high quality hill oil could allow for its incorporation into a broad range of previously unusable products. Research already performed with fish and algal PUFA's could allow for rapid improvements in krill oil stability.

Several spray-dry technologies exist seeking to minimize PUFA oxidation; however ingredients used for stabilisation are themselves allergenic (milk and lactose-based), which are not suitable for various food applications, infant formulae or hypoallergenic applications. Furthermore, previous attempts to encapsulate PUFA's have failed due to the generation of high amounts of un-encapsulated oil and subsequent oxidation products during shelf life, in addition to undesirable particle size for incorporation into food matrices.

In summary, krill and fish oils present difficulties in terms of their use in foods and food supplements due to their taste, odour and oxidative instability. It is an object of the invention to overcome at least one of the above-referenced problems.

STATEMENTS OF INVENTION

The Applicant has addressed the problem of taste, odour and oxidative instability of oil by providing the oil in the form of a core-shell microcapsule, in which the oil (lipid) is provided as lipid emulsion containing denatured or hydrolysed protein and carbohydrate in sufficient amounts to stabilize the emulsion and prevent separation (carbohydrate) and have an anti-oxidant effect (denatured protein/hydrolysed protein), and in which the shell is formed from chitosan which has been found to provide for a very tightly knit core membrane having natural anti-oxidant properties and that is capable of surviving gastric transit yet capable of break down/digestion in the ileum. In particular, inclusion of carbohydrate in the lipid emulsion, in combination with the use of chitosan as a shell-forming material, has been shown to inhibit oxidation of polyunsaturated fatty acids (PUFA's) contained within the emulsion and thereby increase stability during accelerated storage conditions (See FIGS. 6 to 8). Moreover, inclusion of denatured or hydrolysed protein in the core emulsion, in combination with use of chitosan as a shell-forming material, has been shown to inhibit oxidation of polyunsaturated fatty acids (PUFA's) contained within the emulsion and thereby increase stability during accelerated storage (See FIGS. 9 to 10). In addition, the chitosan shell has been found to successfully mask any odour or taste of the lipid—this is especially important when the lipid is a marine-derived lipid such as krill oil or fish oil. Moreover, the provision of the emulsion core as a micro-emulsion provides for improved stability of the emulsion upon release in the mammalian gut.

In a first aspect, the invention provides a gelated mononuclear microencapsulate comprising a lipid emulsion core encapsulated within a gastro-resistant, ileal sensitive, polymerized chitosan membrane shell, wherein the lipid emulsion core typically comprises denatured protein and carbohydrate.

In a further aspect, the invention provides a gelated mono-nuclear microencapsulate comprising a lipid emulsion core encapsulated within a gastro-resistant, ileal sensitive, polymerized chitosan membrane shell, wherein the lipid emulsion core typically comprises hydrolysed protein and carbohydrate.

In one embodiment of the invention, the emulsion is an oil in water (O/W) emulsion. In one embodiment of the invention, the emulsion is a micro-emulsion, and typically comprises a surfactant and a co-surfactant. In one embodiment of the invention, the emulsion is a micro-emulsion and comprises at least two carbohydrates, for example sucrose and a maltodextrin. In one embodiment of the invention, the micro-emulsion is a SMEDDS type system (Self Micro Emulsifying Drug Delivery System).

In one embodiment of the invention, the lipid is a marine derived lipid. In one embodiment of the invention, the marine derived lipid is fish oil. In one embodiment of the invention, the marine derived lipid is hill oil. In one embodiment of the invention, the marine derived lipid is an algal oil. In one embodiment of the invention, the marine derived lipid is a mixture of two or three of fish oil, krill oil, and algal oil. In one embodiment of the invention the lipid comprises (or is enriched in) phospholipid, polyunsaturated fatty acid and an antioxidant. In one embodiment of the invention, the marine derived lipid is a purified polyunsaturated fatty acid. In one embodiment of the invention, the lipid is acid-cleaned lipid. In one embodiment of the invention, the lipid is cleaned marine-derived lipid. In one embodiment of the invention, the lipid is a fatty acid, for example a purified fatty acid. The fatty acid may be an essential or non-essential fatty acid. In one embodiment, the fatty acid is a polyunsaturated fatty acid. In one embodiment, the fatty acid is DHA or ARA. In one embodiment, the lipid is derived from an animal source. In one embodiment, the one embodiment, the lipid is derived from a vegetable source. In one embodiment, the lipid is derived from eggs. In one embodiment, the lipid is derived from seeds. In one embodiment, the lipid is derived from pulses.

In one embodiment of the invention, the carbohydrate is a polysaccharide. In one embodiment of the invention, the carbohydrate is a glucose-containing polysaccharide. In one embodiment, the polysaccharide is maltodextrin. In one embodiment of the invention, the carbohydrate is a disaccharide. In one embodiment of the invention, the polysaccharide is a glucose-containing disaccharide. In one embodiment of the invention, the glucose-containing disaccharide is sucrose or maltose. Typically, the carbohydrate has a DE (dextrose equivalence) of 16-20.

In one embodiment of the invention, the shell comprises a co-surfactant. In one embodiment of the invention, the co-surfactant is lecithin. In one embodiment of the invention, the surfactant is a Tween20 or Tween-80.

In one embodiment of the invention, the shell comprises denatured protein. In one embodiment of the invention, the shell comprises hydrolysed protein. In one embodiment of the invention, the shell comprises denatured whey protein.

In one embodiment of the invention, the denatured or hydrolysed protein is a dairy protein. In one embodiment, the denatured or hydrolysed protein is vegetable protein. In one embodiment of the invention, the denatured or hydrolysed protein is a dairy protein and vegetable protein.

In one embodiment of the invention, the dairy protein is milk protein concentrate. In one embodiment of the invention, the dairy protein is whey protein (i.e. whey protein isolate or whey protein concentrate). In one embodiment of the invention, the vegetable protein is pea protein (i.e. pea protein isolate), preferably yellow pea protein.

In one embodiment, the liquid lipid emulsion core comprises 5.5 to 86.0% total solids (w/v).

In one embodiment, the liquid lipid emulsion core comprises 5.5 to 15% protein (w/v).

In one embodiment, the liquid lipid emulsion core comprises 2.0 to 8.5% carbohydrate (w/v).

In one embodiment, the liquid lipid emulsion core comprises 0.01 to 0.5% co-surfactant (v/v).

In one embodiment, the liquid lipid emulsion core comprises 0.01 to 1.1% surfactant (v/v).

Preferably, the microencapsulates are dried, for example vacuum dried. Preferably, the microencapsulates are dried to a water activity (Aw) of 0.2 to 0.3.

The invention also relates to a composition suitable for oral administration to a mammal comprising a multiplicity of microencapsulates of the invention.

Typically, the composition is selected from a food product, a beverage, a food ingredient, an animal feed ingredient, a nutritional supplement, an animal feed supplement, or oral dosage pharmaceutical. In one embodiment of the invention, the composition is an infant formula. In one embodiment, the composition is an infant formula, and in which the lipid is selected from ARA or DHA.

The invention also relates to a microencapsulate of the invention, or a composition of the invention, for use in a method selected from:
   improving cardiovascular health;
   treatment of cardiovascular disease;
   reducing inflammation;
   treatment of an inflammatory condition;
   improving cognitive function; and
   treatment of a disease or condition characterised by reduced cognitive function.

The invention also relates to a method of making a mono-nuclear microencapsulate having a lipid emulsion core encapsulated within a gastro-resistant polymerized chitosan membrane shell, which method employs a double nozzle extruder comprising an outer nozzle concentrically formed around an inner nozzle, the method comprising the steps of:
   co-extruding a core-forming lipid emulsion through the inner nozzle of a double nozzle extruder and a chitosan solution through the outer nozzle of the double nozzle extruder to form mono-nuclear microdroplets; and
   curing the mono-nuclear microdroplets by acidic polymerisation in an acidic gelling bath.

In one embodiment, the core forming lipid emulsion comprises a denatured protein and a carbohydrate. In one embodiment, the core forming lipid emulsion comprises a hydrolysed protein and a carbohydrate.

In one embodiment, the core-forming lipid emulsion is formed by the steps of:
   preparing a lipid in water emulsion;
   preparing a solution of carbohydrate and denatured or hydrolysed protein to a total solids content of 5.5-86.0%;
   admixing the emulsion and solution and homogenising to form the core-forming lipid emulsion.

In one embodiment, the core forming lipid emulsion is a micro-emulsion and typically comprises denatured or hydrolysed protein, carbohydrate, surfactant and co-surfactant. However, it will be appreciated that one of the surfactant or co-surfactant can be contained within the acidic gelling bath, and not initially within the core-forming emulsion. Thus, in one embodiment the core-forming lipid emulsion comprises a surfactant, and the acidic gelling bath comprises a co-surfactant. In another embodiment the core-forming lipid emulsion comprises a co-surfactant, and the acidic gelling bath comprises a surfactant. In another embodiment the core-forming lipid emulsion comprises both a co-surfactant and a surfactant.

In one embodiment, the core-forming lipid emulsion is formed by the steps of:
preparing a lipid in water emulsion at a ratio of 1:1 to 1:2;
preparing a solution of carbohydrate, denatured or hydrolysed protein, optionally surfactant and optionally co-surfactant to a total solids content of 5.5-86.0%;
admixing the emulsion and solution and homogenising to form the core-forming lipid microemulsion.

In one embodiment, the carbohydrate is allowed to fully hydrate in solution prior to addition of the denatured or hydrolysed protein. Typically, this is achieved by agitating a carbohydrate solution/slurry, typically at an elevated temperature.

In one embodiment, the chitosan solution is an acidic solution and typically comprises about 1% chitosan (w/v)—for example from 0.5% to 1.5% chitosan. In one embodiment, the chitosan solution comprises about 0.8% to 1.2% chitosan (w/v). In one embodiment, the chitosan solution comprises a co-surfactant. In one embodiment, the chitosan solution comprises a co-surfactant in an amount of 0.01% to 0.1% (w/v), preferably 0.01 to 0.05%. In one embodiment, the chitosan solution comprises lecithin in an amount of 0.01% to 0.1% (w/v), preferably 0.01 to 0.05%. In one embodiment, the acid is acetic acid, although other weak acids may be employed. In one embodiment, the chitosan solution is left for at least 6, preferably 12, hours to de-aerate. In one embodiment, the chitosan is a chitosan derivative—various chitosan derivatives are described in the literature (N. M. Alves, International Journal of Biological Macromolecules, Vol. 43, Issue 5, December 2008; M. Prabaharan, J. Biomater Appl 2008 Jul. 23 (1)). In one embodiment of the invention, an alternative shell-forming material is employed, for example an alternative hydrocolloid biopolymer. In one embodiment, the chitosan solution comprises denatured or hydrolysed protein. In one embodiment, the chitosan solution comprises denatured or hydrolysed whey protein.

In one embodiment, the lipid is acid cleaned prior to formation of the oil-in-water (O/W) emulsion. This generally comprises washing the lipid in strong acid for a suitable period of time to break down any proteinaceous matter in the lipid. Example of strong acid are HCl, $H_2SO_4$, $HNO_3$, $HClO_3$ and $HIO_4$. Preferably, the cleaned lipid is neutralised after leaning (i.e. the pH is adjusted to about pH 7-7.5 or thereabouts).

In one embodiment, the core-forming lipid emulsion comprises:
5.5-15.0% denatured protein (w/v);
2.0-8.5% carbohydrate (w/v);
15-66.5% lipid (v/v);
optionally, 0.01-1.1% surfactant; and
optionally, 0.01-0.5% co-surfactant.

In one embodiment, the core-forming lipid emulsion comprises:
5.5-15.0% hydrolysed protein (w/v);
2.0-8.5% carbohydrate (w/v);
15-66.5% lipid (v/v);
optionally, 0.01-1.1% surfactant; and
optionally, 0.01-0.5% co-surfactant.

In one embodiment, the acidic gelling bath comprises a suitable buffer and an acidic pH capable of gelling the microdroplets into gelated microcapsules. In one embodiment, the buffer is an acetate buffer. In one embodiment, the acidic gelling bath comprises chitosan (0.04-0.1.3% (w/v)). In one embodiment, the acidic gelling bath comprises a co-surfactant (0.01-0.5% (w/v). In one embodiment, the acidic gelling bath is heated.

In one embodiment, the inner and/or outer nozzles are heated, for example to at least 40° C., 50° C. or 60° C.

In one embodiment of the invention, the process includes a step of drying the microencapsulates. In one embodiment of the invention, the process includes a step of drying the microencapsulates to a water activity (Aw) of 0.2 to 0.3.

The invention also relates to an emulsified composition suitable for use as a core-forming material in microcapsules of the type having a core-shell morphology and made using a double nozzle extruder, the emulsified composition comprising:
5.5-15.0% denatured protein (w/v);
2.0-8.5% carbohydrate (w/v);
15-66.5% lipid (v/v);
optionally, 0.01-1.1% surfactant; and
optionally, 0.01-0.5% co-surfactant.

The invention also relates to an emulsified composition suitable for use as a core-forming material in microcapsules of the type having a core-shell morphology and made using a double nozzle extruder, the emulsified composition comprising:
5.5-15.0% hydrolysed protein (w/v);
2.0-8.5% carbohydrate (w/v);
15-66.5% lipid (v/v);
optionally, 0.01-1.1% surfactant; and
optionally, 0.01-0.5% co-surfactant.

Definitions

"Gelated": means formed by gelation in a process in which liquid microdroplets are extruded or sprayed into a gelling bath and immediately cured in a gelling bath. Examples of gelation are described in the literature, for example PCT/EP2010/054846 and PCT/EP2014/062154.

"Mono-nuclear": as applied to the microencapsulate means that the core material is provided as a single core or nucleus surrounded by a membrane shell, and is different to the microbeads described in the prior art, for example PCT/EP2010/054846 and PCT/EP2014/062154, in which the encapsulated material is provided as a multiplicity of discrete droplets distributed throughout a continuous matrix of encapsulating material. The use of mono-nuclear microencapsulates allows greater amounts of core material to be encapsulated compared to single nozzle microbead formation and additionally allows the shell material "shield" the core material from the environment, which is important when the core contains lipid prone to oxidation.

"Microencapsulate": means a mononuclear core/shell type structure having an average dimension in the range of 20-2000 microns, preferably 80-1200 microns as determined using a method of laser diffractometry (Mastersizer 2000, Stable Micro Systems, Surrey, UK). This method is determines the diameter, mean size distribution and D (v, 0.9) (size at which the cumulative volume reaches 90% of the total volume), of micro-encapsulates with diameters in the range of 0.2-2000 μm. For microencapsulate size analysis, micro-encapsulate batches were re-suspended in Milli-Q water and size distribution is calculated based on the light intensity distribution data of scattered light. Measurement of microencapsulate size is performed at 25° C. and six runs are performed for each replicate batch (Doherty et al., 20111) (*Development and characterisation of whey protein microbeads as potential matrices for probiotic protection*, S. B. Doherty, V. L. Gee, R. P. Ross, C. Stanton, G. F. Fitzgerald, A. Brodkorb, *Food Hydrocolloids* Volume 25, Issue 6, August 2011, Pages 1604-1617). Preferably, the microencapsulate is substantially spherical as shown in the attached figures. Typically the microencapsulate has a monodispersed matrix and even membrane thickness (which means that the components of the microcapsule are extruded using a two-phase system). This is distinct and different from microparticles having a homgenous matrix, single phase morphology.

"Gastro-resistant": means that the microencapsulates can survive intact for at least 60 minutes in the simulated stomach digestion model described in Minekus et al., 1999 and 2014 (*A computer-controlled system to simulate conditions of the large intestine with peristaltic mixing, water absorption and absorption of fermentation product*, Minekus, M., Smeets-Peeters M, Bernalier A, Marol-Bonnin S, Havenaar R, Marteau P, Alric M, Fonty G, Huis in't Veld JH, *Applied Microbiology Biotechnology*. 1999 December; 53 (1):108-14) and (Minekus et al., 2014, *A standardised static in vitro digestion method suitable for food—an international consensus*, Minekus, A. et al., *Food Function*, 2014, 5, 1113).

"Ileal-sensitive": means that the microencapsulates are capable of releasing their contents in vivo in the ileum of a mammal.

"Protein" means any protein susceptible to thermal or enzymatic denaturation, for example dairy protein or vegetable protein, or a mixture of dairy protein or vegetable protein. Preferably, the protein is a globular protein.

"Denatured": means partially or fully denatured. Preferably at least 90%, 95% or 99% of the protein is denatured. A method of determining the % of denatured protein is provided below. Denatured protein was removed by acid precipitation using an acetic acid buffer pH 4.6 followed by centrifugation at 20,000 g for 20 minutes. Ju and Kilara (1998) claimed that at pH 4.6 some native whey proteins formed aggregates. This did not occur in this presented invention as no protein precipitated when the protein was unheated, (TO), sample was adjusted to pH 4.6. (Ju, Z. Y., & Kilara, A. (1998). *Gelation of Ph-Aggregated Whey Protein Isolate Solution Induced by Heat, Calcium Salt and Acidulant. Journal of Agricultural and Food Chemistry*, 46(5), 1830-1835).

The supernatant was diluted and the native protein concentration was determined using reverse phase HPLC using a Source and 5RPC column (Amersham Biosciences UK limited). The HPLC system consisted of a Waters 2695 separation module with a Waters 2487 dual wavelength absorbance detector. The data were acquired and processed using Waters empower software (Milford, Mass., USA).

The protein denaturation rate is related to the reaction order by the following equation: $dC/dt = kC^n$ ... where k is the reaction rate, n is the reaction order and C the concentration of native protein. This equation can be integrated to give $$(C_t/C_0)^{1-n} = 1 + (n-1)kt \text{ (for } n>1),$$

Where Ct is the native β-Lg concentration at time t, $C_0$ is the initial β-Lg concentration. Further rearranging gives:

$$C_t/C_0 = [1+(n-1)kt]^{1/1-n}$$

The natural log of this equation was taken:

$$\ln(C_t/C_0) = [1/1-n] \ln [1+(n-1)kt]. \quad \text{(Equation 1)}$$

Logging decay data such as this equalises the data per unit time and reduces error when solving the equations. The reaction orders and rates were determined by fitting the experimental data to Equation 1. All experimental points were included in the curve fit; this is reasonable considering the rapid heating-up time of the protein solution. Introducing a lag-time to the data did not significantly alter the results obtained. The data were also fitted to the first order decay equation $$\ln(C_t/C_0) = -kt \quad \text{(Equation 2)}$$

to rule out the possibility of first order kinetics.

"Hydrolysed" means any protein that has been hydrolysed to at least partially break up the protein into smaller peptide or polypeptides. It can be fully or partially hydrolysed. The degree of hydrolysis (% DH) may be variable and can be determined by routine experimentation. Typically, the protein is hydrolysed to a degree of from 10% to 99%, typically, from 15% to 95%, typically from 20% to 65%, suitably 45%. Degree of hydrolysis (DH) is defined as the proportion of cleaved peptide bonds in a protein hydrolysate, and may be determined using the OPA spectrophotometric assay, which involve the using N-acetyl-L-Cysteine (NAC) as the thiol reagent. One means to determine % DH is using a method of hydrolysis of proteins performed at high temperatures and for short times with reduced racemization in order to determine the enantiomers of D and L amino acids, Csapo, J. et al., Acta Univ, Sapientiae, Alimentaria, 2008; pg 31-48. Methods of hydrolysis are known to a person skilled in the art and include thermal and proteolytic hydrolysis.

"Dairy protein" means any protein source isolated from expressed from the mammary glands of a female mammal. Dairy proteins include Milk protein concentrate or isolates (MPC or MPI)—Milk protein concentrates are produced by ultrafiltration (UF) of milk—or whey protein concentrates or isolates or caseinates. The product in liquid form is generally referred to as UF milk while the dry form is known as MPC. This product contains unaltered forms of both casein and whey protein. The level of protein, lactose and mineral present vary depending on the degree of protein concentration.

"Vegetable protein" means any protein isolated and/or extracted from a herbaceous plant with parts that are typically used as a source of food for mammals. Sources include, soy, pea, rice, hempseed, quinoa, various grains (i.e. wheat) and nut sources. In one embodiment, the vegetable protein is pea protein isolate (PPI).

"Pea protein" should be understood to mean protein obtained from pea, typically total pea protein. Preferably the pea protein is pea protein isolate (PPI), pea protein concentrate (PPC), or a combination of either. Typically, the liquid core comprises 6-8% pea protein, ideally 6.6-7.5% (w/v). Typically the solvent for the pea protein has a pH of greater than 10 or 10.5. Ideally, the pea protein is solubilised in an alkali solvent.

"Lipid" means triglycerides, monoglycerides, diglycerides, phospholipids, fatty acids (essential or non-essential), oils, or compositions enriched in such lipids such as fish oils, krill oil, algal oil, purified fatty acid compositions (for example purified LC-PUFA's, DHA or ARA) and which may contain phospholipids, antioxidants and other fat-soluble components such as fat-soluble vitamins. In one embodiment, the lipid is a purified fatty acid. "Fatty acids" are classified based on the length and saturation characteristics of the carbon chain. Fatty acids include fatty acids in various forms, including but not limited to triacylglycerols, diacylglycerols, monoacylglycerols, phospholipids, free fatty acids, esterified fatty acids, and natural or synthetic derivative forms of these fatty acids (e.g. calcium salts of fatty acids, ethyl esters, etc). Short chain fatty acids have 2 to about 7 carbons and are typically saturated. Medium chain fatty acids have from about 8 to about 17 carbons and may be saturated or unsaturated. Long chain fatty acids have from 18 to 24 or more carbons and may also be saturated or unsaturated. In longer chained fatty acids there may be one or more points of unsaturation, giving rise to the terms "monounsaturated" and "polyunsaturated," respectively. The lipid may be derived from any source, for example fish, algae, krill, animals, vegetables, egg, nuts and seeds.

In one embodiment, the lipid is a PUFA, preferably a long-chain PUFA (LC-PUFA). "LC-PUFAs" are categorized according to the number and position of double bonds in the fatty acids according to a well understood nomenclature. There are two common series or families of LC-PUFAs, depending on the position of the double bond closest to the methyl end of the fatty acid: the n-3 (or ω-3 or omega-3) series contains a double bond at the third carbon, while the n-6 (or ω-6 or omega-6) series has no double bond until the sixth carbon. Examples of LC-PUFA's include DHA and EPA. "Docosahexaenoic acid" ("DHA") refers a fatty acid with a chain length of 22 carbons with 6 double bonds beginning with the third carbon from the methyl end and is designated "22:6 n-3". "Eicosapentaenoic acid" ("EPA") which is designated "20:5 n-3" and docosapentaenoic acid n-3 ("DPA(n-3)") which is designated "22:5 n-3." "Arachidonic acid" ("ARA") which is designated "20:4 n-6" and docosapentaenoic acid n-6 ("DPAn-6") which is designated "22:5 n-6" are suitable.

"Lipid emulsion" means an oil-in-water emulsion in which the lipid (oil) forms a discontinuous phase dispersed within an aqueous phase. Typically, the ratio of lipid to aqueous phase is 1:1 to 1:3 or 1:2. Typically, the lipid emulsion is a microemulsion. Preferably, the emulsion is stable (for example, as shown below in FIG. 3). Preferably, the lipid emulsion comprises at least 30% lipid (v/v). Preferably, the lipid emulsion comprises at least 40% lipid. Preferably, the lipid emulsion comprises at least 50% lipid. Preferably, the lipid emulsion comprises 50-65% lipid. Preferably, the lipid emulsion comprises 15-65% lipid. Preferably, the lipid emulsion comprises 30-50% lipid. Preferably, the lipid emulsion comprises 35-45% lipid (all v/v). Preferably, the lipid emulsion comprises 5.5-15% protein. Preferably, the lipid emulsion comprises 8-12% protein. Preferably, the lipid emulsion comprises about 9-11% protein (all w/v). Preferably, the lipid emulsion comprises 2-8.5% carbohydrate. Preferably, the lipid emulsion comprises 3-7% carbohydrate. Preferably, the lipid emulsion comprises about 4-6% carbohydrate (all w/v). Preferably, the lipid emulsion (or gelling bath) comprises 0.01-1.1% surfactant. Preferably, the lipid emulsion (or gelling bath) comprises 0.01-0.5% surfactant. Preferably, the lipid emulsion (or gelling bath) comprises about 0.1-0.5% surfactant. Preferably, the lipid emulsion (or gelling bath) comprises 0.01-0.5% co-surfactant. Preferably, the lipid emulsion (or gelling bath) comprises 0.1-0.5% co-surfactant. Preferably, the lipid emulsion (or gelling bath) comprises about 0.1-0.3% co-surfactant.

"Stable emulsion" refers to a mixture that does not experience phase separation as a function of time. The stability of the Krill/protein/CHO emulsion feed to the encapsulator was determined using an accelerated dispersion stability analyser (LUMiFuge 116 stability analyser, L. U. M. GmbH, Berlin, Germany), whereby 4 mL aliquots were placed in polycarbonate sample cells (type 110-131 xy) and centrifuged at ~1500 rpm for 24 h at 4, 25, and 32° C., with transmission profiles measured every 90 s. The charge coupled device (CCD) line sensor received light transmitted through the sample, which showed a pattern of light flux as a function of the radial position, giving a macroscopic fingerprint of the sample at a given time, from which Krill emulsion instability, such as sedimentation, flocculation or particle aggregation could be detected. The sedimentation rate ($mmd^{-1}$) was determined from the plot of position against time using Sepview 4.1 (L. U. M. GmbH) software. The threshold (the position of light transmission on the y-axis that was most representative of the movement of the interface over the measurement time) was set at 20%. Analysis of variance (ANOVA): performed using Minitab 15 (Minitab Ltd, Coventry, U K, 2007) statistical analysis package and the effects of replicates were estimated for response variable i.e. temperature & time. The level of significance was determined at $P<0.05$.

"Microemulsion" means a lipid emulsion that is formed between lipid, an aqueous phase and a surfactant and optionally a co-surfactant. In one embodiment, the microemulsion comprises lipid, an aqueous phase and two carbohydrates, for example maltodextrin and sucrose. It is a generally clear (non-turbid) and thermodynamically stable emulsion that does not require high shear for its formation. Typically, the microemulsion is a SMEDDS.

"Carbohydrate" means a monosaccharide, disaccharide, oligosaccharide or polysaccharide, or mixtures or derivatives thereof. Typically, the carbohydrate has a dextrose equivalency (DE) of 16-20. Examples of carbohydrates include sucrose and maltodextrin. "Disaccharide" means a sugar molecule comprising two linked saccharide units, for example sucrose, maltose, trehalose or the like. Preferably, the disaccharide is sucrose or maltose.

"Polymerised": as applied to the chitosan membrane shell means that the chitosan is crosslinked as a result of gelation in an acidic gelling bath. Preferably, the polymerized chitosan forms a water and/or air impermeable shell.

"Rested" means leaving the chitosan solution rest for a period of time to allow the chitosan to de-aerate. Generally, the chitosan solution is allowed to rest for at least 4, 6, 8, 10 or 12 hours. Typically, the chitosan solution is rested at room temperature. Preferably, the chitosan is fully hydrated.

"Acidic gelling bath" means a bath having an acidic pH that is capable of polymerising or gelling the droplets. Typically, the acidic gelling bath has a pH of less than 5, for example 3.5 to 4.7, 3.8 to 4.6, or 3.8 to 4.4. The acidic gelling bath is generally formed from an acid buffer, for example acetic acid buffer. Typically, the acidic gelling bath has an acid concentration of 0.1M to 0.8M, preferably 0.3M to 0.7M, and more preferably 0.4M to 0.6M. In one embodiment, the acidic gelling bath comprises surfactant. In one embodiment, the acidic gelling bath comprises 0.01 to 1.1% surfactant or co-surfactant or both. In one embodiment, the surfactant is a hydrophilic surfactant. In one embodiment, the surfactant is a TWEEN (Tween-20 or Tween-80) surfactant.

"Double nozzle extruder" means an apparatus comprising an outer nozzle concentrically arranged around an inner nozzle, and in which the denatured or hydrolysed protein solution is extruded through the outer nozzle and the core-forming solution is extruded through the inner nozzle to form microdroplets which are gelled in the gelling bath. Examples of double nozzle extruders include instrumentation provided by BÜCHI Labortechnik (www.buchi.com) and GEA NIRO (www.niro.com).

"Cured mono-nuclear microdroplets in the acidic gelling bath" means that the microdroplets are allowed remain in the gelling bath for a period of time sufficient to cure (harden) the microbeads. The period of time varies depending on the microdroplets, but typically a curing time of at least 10, 20, 30, 40 or 50 minutes is employed.

"Viscosity" means the resistance to flow of fluids. The most commonly used unit is the centipoise. Increasing viscosity tends to increase droplet size. For some nozzle designs, increasing the viscosity tends to increase the flow rate.

"Astaxanthin" is defined as a very potent antioxidant with anti-inflammatory properties and the ability to cross the blood-brain barrier [59,60]. It can neutralize free radicals, which are unstable molecules that can damage cells and increase the risk for age-related diseases, cancer, and heart disease. Astaxanthin has been associated with protecting lipids and low-density lipoproteins (LDL) from oxidation.

"Particle Size" means the size of a spherical particle expressed as the diameter measurement. For non-spherical particles, the size can be represented as an apparent diameter.

"Size distribution" relates to the fact that droplets and particles that are produced in a spray dryer are never of one particular size. Any nozzle will produce both large and small droplets.

The dryer must operate so that it is able to dry the largest droplet without scorching the smallest one. Size distributions can be represented by a cumulative distribution curve. Particle size distributions were measured with a Nicomp model 380 ZLS particle size system (Nicomp PSS, Santa Barbara, Calif., USA). Measurements were taken at 23° C. using a 635 nm source and a scattering angle of 90°. Samples were prepared for measurement by dilution in deionized water. calorimetry data were collected with a TA Instruments model Q20 differential scanning calorimeter (TA Instruments, New Castle, Del., USA). The instrument was calibrated with an Indium standard. Aluminium sample pans were used and samples were scanned at 5° C./min over the temperature range of 25° C. to 90° C.

BRIEF DESCRIPTION OF THE FIGURES

FIG. 1. Compositional difference between Krill oil and algae fish oils.

FIG. 2. Physico-chemical characteristics of formulations generated in the presence and absence of Tryglycerides.

DETAILED DESCRIPTION OF THE INVENTION

Figure 3:
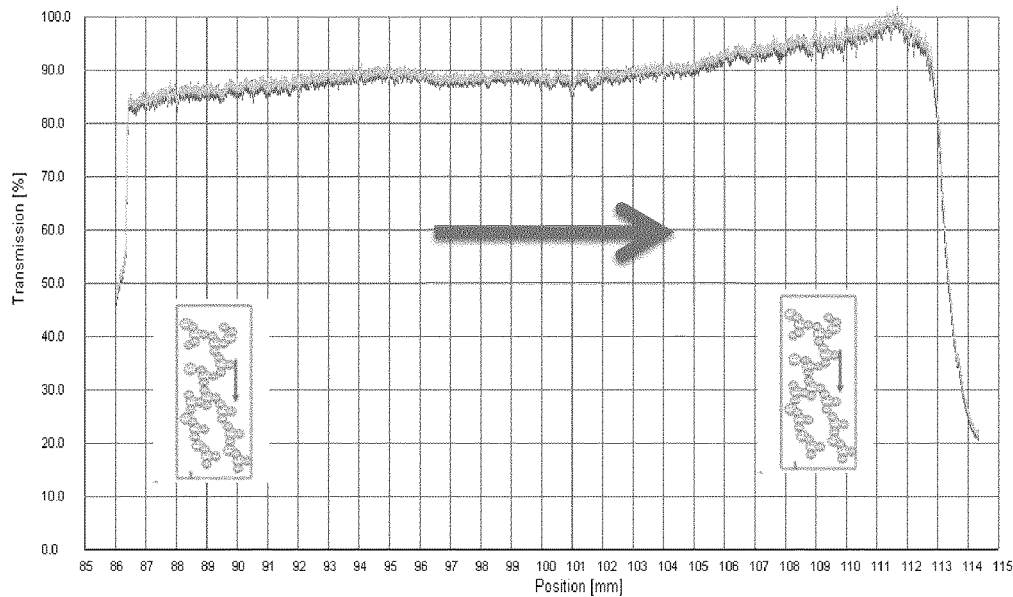
FIG. 3. LumiFuge analysis to verify the stability of the feed to the encapsulator.
Figure 3:
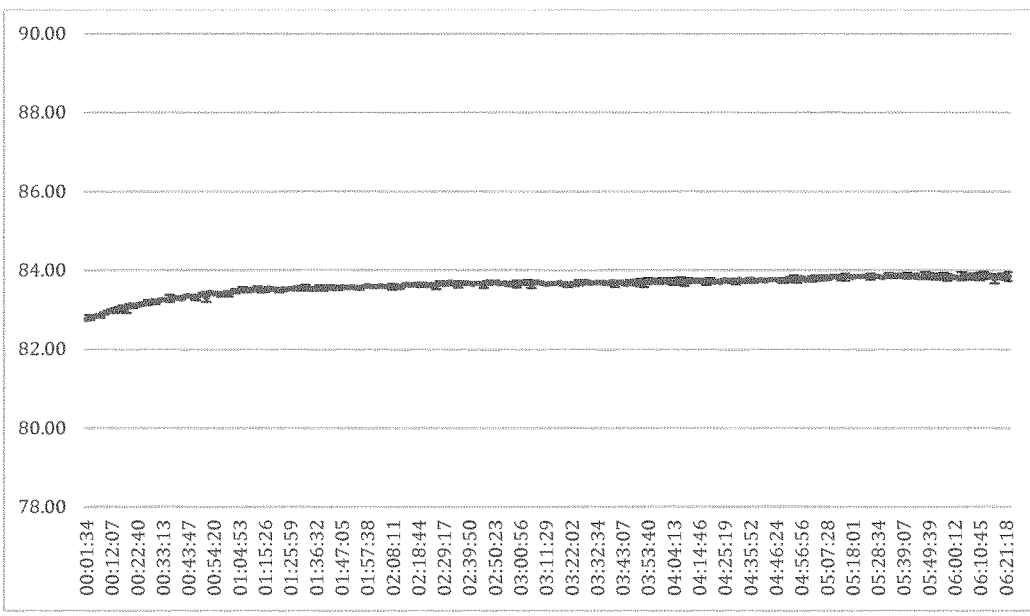
Figure 4:
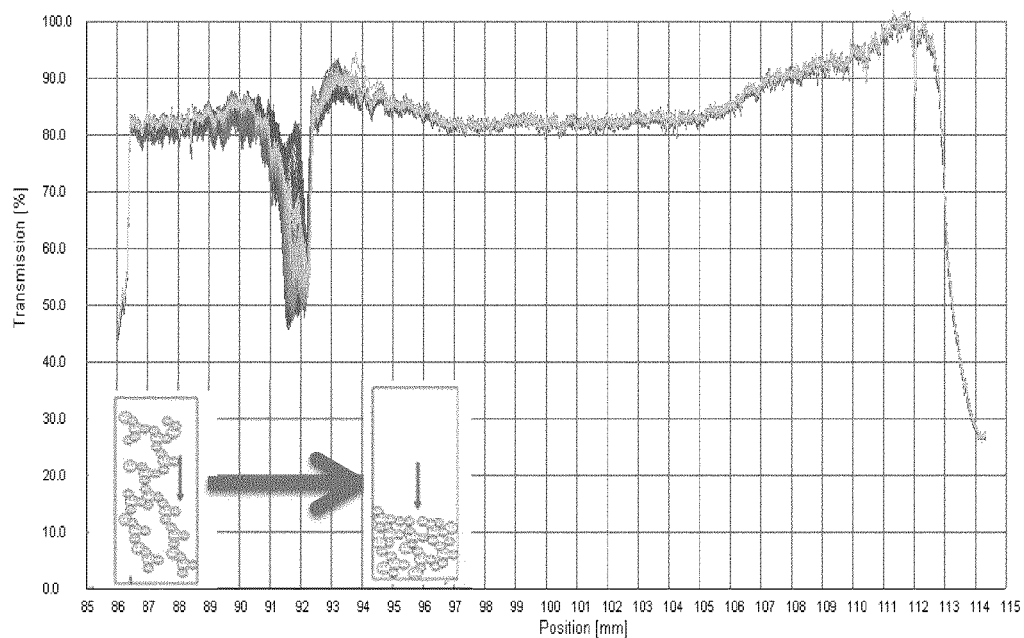
FIG. 4. LumiFuge analysis to verify the instability of the feed to the encapsulator when an incorrect Krill/protein/CHO emulsion is prepared.
Figure 4:
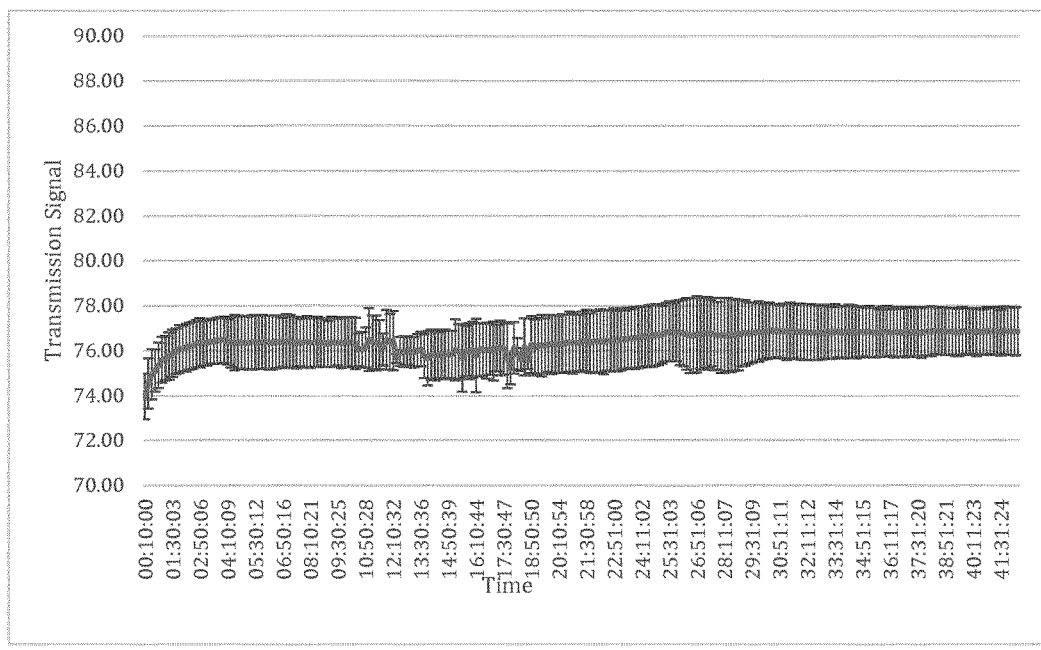

In accordance with the present description, there is now provided a process for deodorization of marine extracted oils involving the encapsulation of tryglycerides and/or phospholipids, choline or astaxanthin. The process consists of the following steps: i) washing said marine extracted oil with a strong acid (HCl, $H_2SO_4$, $HNO_3$, $HClO_3$ and $HIO_4$). The most preferred strong acid is however HCl. Following this step, the washed extract is emulsified in the presence of a vegetable protein (pea protein), carbohydrate (maltodextrin DE 16-20), and a hydrophilic surfactant (Tween-80). The presented invention is then coextruded in the presence of chitosan to generate micro-capsules. This microencapsulation food system comprises: a masked and/or deodorized marine oil achieved using a food grade, acceptable carrier. This formulation also represents a SMEEDS system due to the presence of an oil, surfactant and co-surfactants, which i) improves palatability but also increases oil bioavailability. Hence, this encapsulated system represents a stable format for LCFA's and hill oils that reduces oxidative stress, extend shelf life, improve bioavailability and taste, allowing to broaden product applications for previously unstable fat blends. Oil loading capacity is approx. 50-61% extract, which is significantly higher relative to standard industrial (approx. 20-25%). Furthermore, this novel technology utilizes a non-dairy and non-allergenic ingredient for stabilization of DHA and ARA, which is permitted for use as an additive for food and infant formulae applications.

Materials for Propose SMEDDS Formulation:
  Bioactive Extract: Fish oil or krill oil or any other oil extract
  Proteins: pea protein or milk protein i.e.PPI or WPI
  Surfactants: Hydrophilic surfactants i.e. Tween-80
  Co-surfactant: Lecithin or Labrasol
  Carbohydrate: Maltodextrin i.e. DE 16-20
  Hydrocolloid: Chitosan (High Molecular weight, 600 kDa)
Methods
Method 1
  Day 1.
  Prepare 13% total solids solution using milk protein concentrate (MPC)
  Allow protein to hydrate overnight at 4° C., pH 7.5
  Take Krill oil extract and mix strong acid (HCl; 2M) with krill oil extract
  Agitate at 40° C. for 30 minutes
  Wash extract with sterile water until the pH is reverts at neutral conditions (pH 7.5)
  Adjust using NaOH (0.1M) or HCL (0.2M) if necessary at room temperature.
  Maintain at 4° C. overnight
  Prepare a chitosan solution in 0.09% (v/v) acetic acid using and Ultra Turrax, sonicate for 30 sec to remove air pockets and maintain at 4° C. overnight.

Day 2.
Prepare a suspension of krill extract in water (1:1.5 ratio)
Homogenise using and Ultra Turrax (T25) speed 11,000 rpm for 3 minutes at 4° C. This represents the Krill Oil emulsion (O/W)
Pre-heat Milk Protein Concentrate (MPC) to 65° C.
Heat treat to 95° C. for 1 minutes at pH 7.5 using a microthermics/UHT unit
Cool suspension of soluble protein aggregates to 4° C. and hold for 3 hours (no agitation). This represents the heat denatured protein suspension
Prepare a 7% Maltodextrin (MD) solution (DE 16-20) with lecithin (0.03% W/v) in water
Agitate at 65° C. for 30 minutes until fully hydrated
Admix the denature protein solution with heated Maltodextrin to achieve an 11% solution (total solids basis).
Homogenise using an Ultrax Turrax for 1 minute at 65° C.
Add hill oil extract and homogenise again for using an Ultrax Turrax (T25) for 4 minute at 65° C. This represents the Krill/protein/MD emulsion
Mono-nuclear microcapsules were prepared using the co-extrusion laminar jet break-up technique. The encapsulator was fitted with two different sized concentric nozzles (internal and external).
Krill/protein/MD emulsion dispersions are supplied to the internal nozzle using an air pressure regulation system which enabled flow rates of 6-10 L/min to be generated using a maximum head pressure of 0.9-1.1 bar.
The external phase (chitosan alone) is supplied using a precision syringe pump connected to the outer nozzle to flow rates of between 13 and 20 L/min.
Spherical microcapsules are obtained by the application of a set vibrational frequency, with defined amplitude, to the co-extruded liquid jet consisting of outer layer of heat-treated protein material and inner core consisting of Krill/protein/MD emulsion
The material in the inner and outer nozzle are both heated to 65° C. in order to allow for better flowability in commercial operations.
The resulting concentric jet breaks up into microcapsules, which fall into a magnetically stirred gelling bath 20 cm below the nozzle.
The gelling bath consisted of 0.3M acetic acid, 0.3 M sodium acetate, and 0.09% chitosan (high molecular weight) and 0.02% Tween-80. Temperature is maintained at 40° C.
Microcapsules are recovered after 30 minutes polymerisation in the buffer bath and washed in water
Microcapsules are then vacuum dried at 40° C. to a final moisture content of 4%.

Method 2
Day 1.
Prepare 11% total solids solution using whey protein isolate (WPI)
Allow protein to hydrate overnight at 4° C., pH 7.5
Take Krill oil extract and mix strong acid (HCl; 2M) with krill oil extract
Agitate at 40° C. for 30 minutes
Wash extract with sterile water until the pH is reverts at neutral conditions (pH 7.5)
Adjust using NaOH (0.1M) or HCL (0.2M) if necessary at room temperature.
Maintain at 4° C. overnight.
Prepare a chitosan solution in 1.1% (w/v) acetic acid using and Ultra Turrax, sonicate for 30 sec to remove air pockets and maintain at 4° C. overnight.

Day 2.
Prepare a suspension of Krill extract in water (1:2 ratio)
Homogenise using and Ultra Turrax (T25) speed 11,000 rpm for 3 min at 4° C. This represents the Krill Oil emulsion (O/W)
Pre-heat WPI to 65° C.
Heat treat to 85° C. for 1 min at pH 7.5 using a microthermics/UHT unit
Cool suspension of soluble protein aggregates to 4° C. and hold for 1 hour (no agitation). This represents the heat denatured protein suspension.
Hydrate sucrose (based on 9.2% total solids) with lecithin (0.03% W/v) in water
Agitate at 65° C. for 30 minutes until fully hydrated
Admix the denatured protein solution with sucrose to achieve an 10.1% solution (total solids basis).
Agitate using an overhead paddle for 5 min at 65° C.
Add Krill oil extract and homogenise using an Ultrax Turrax (T25) for 4 minute at 65° C. This represents the Krill/protein/sucrose emulsion
Mono-nuclear microcapsules were prepared using the co-extrusion laminar jet break-up technique. The encapsulator was fitted with two different sized concentric nozzles (internal and external).
Krill/protein/sucrose emulsion dispersions are supplied to the internal nozzle using an air pressure regulation system which enabled flow rates of 6-10 L/min to be generated using a maximum head pressure of 0.9-1.1 bar.
The external phase (Chitosan alone, 1.10% w/v) is supplied using a precision syringe pump connected to the outer nozzle to flow rates of between 13 and 20 L/min.
Spherical microcapsules are obtained by the application of a set vibrational frequency, with defined amplitude, to the co-extruded liquid jet consisting of outer layer of chitosan material and inner core consisting of Krill/protein/sucrose emulsion.
The material in the inner and outer nozzle are both heated to 65° C. in order to allow for better flowability in commercial operations.
The resulting concentric jet breaks up into microcapsules, which fall into a magnetically stirred gelling bath 20 cm below the nozzle.
The gelling bath consisted of 0.3M acetic acid, 0.3 M sodium acetate and 0.02% Tween-80. Temperature is maintained at 40° C.
Microcapsules are recovered after 15 minutes polymerisation in the buffer bath and washed in water
Microcapsules are then vacuum dried at 40° C. to a final moisture content of 4%.

Method 3
Day 1.
Prepare 13% total solids solution using milk protein concentrate (MPC)
Allow protein to hydrate overnight at 4° C., pH 7.5
Take DHA/ARA and mix with strong acid (HCl; 2M)
Agitate at 40° C. for 30 minutes
Wash extract with sterile water until the pH is reverts at neutral conditions (pH 7.5)
Adjust using NaOH (0.1M) or HCL (0.2M) if necessary at room temperature.
Maintain at 4° C. overnight
Prepare a chitosan solution in 0.085% (v/v) acetic acid using and Ultra Turrax, sonicate for 30 sec to remove air pockets and maintain at 4° C. overnight.

Day 2.

Prepare a suspension of DHA/ARA in water (1:1.5 ratio)

Homogenise using and Ultra Turrax (T25) speed 11,000 rpm for 3 minutes at 4° C. This represents the DHA/ARA emulsion (O/W)

Pre-heat Milk Protein Concentrate (MPC) to 65° C.

Perform a two-stage hydrolysis process using a trypsin preparation with a heat-treatment step (from 3 to 10 min at 80 to 100° C.) between the two hydrolysis steps.

Cool the suspension of hydrolysed protein to 4° C. and hold for 3 hours (no agitation). This represents the hydrolysed protein suspension Prepare a 7% Maltodextrin (MD) solution (DE 16-20) with lecithin (0.03% W/v) in water Agitate at 65° C. for 30 minutes until fully hydrated Admix the hydrolysed protein solution with heated Maltodextrin to achieve an 11% solution (total solids basis).

Homogenise using an Ultrax Turrax for 1 minute at 65° C.

Add DHA/ARA extract and homogenise again for using an Ultrax Turrax (T25) for 4 minute at 65° C. This represents the DHA/ARA/protein/MD emulsion Mono-nuclear microcapsules were prepared using the co-extrusion laminar jet break-up technique. The encapsulator was fitted with two different sized concentric nozzles (internal and external).

DHA/ARA/protein/MD emulsion dispersions are supplied to the internal nozzle using an air pressure regulation system which enabled flow rates of 6-10 L/min to be generated using a maximum head pressure of 0.9-1.1 bar.

The external phase (chitosan alone) is supplied using a precision syringe pump connected to the outer nozzle to flow rates of between 13 and 20 L/min.

Spherical microcapsules are obtained by the application of a set vibrational frequency, with defined amplitude, to the co-extruded liquid jet consisting of outer layer of heat-treated protein material and inner core consisting of DHA/ARA/protein/MD emulsion The material in the inner and outer nozzle are both heated to 65° C. in order to allow for better flowability in commercial operations.

The resulting concentric jet breaks up into microcapsules, which fall into a magnetically stirred gelling bath 20 cm below the nozzle.

The gelling bath consisted of 0.3M acetic acid, 0.3 M sodium acetate, and 0.09% chitosan (high molecular weight) and 0.02% Tween-80. Temperature is maintained at 40° C.

Microcapsules are recovered after 30 minutes polymerisation in the buffer bath and washed in water Microcapsules are then vacuum dried at 40° C. to a final moisture content of 4%.

Method 4

Day 1.

Prepare 13% total solids solution using milk protein concentrate (MPC)

Allow protein to hydrate overnight at 4° C., pH 7.5

Take krill oil and mix with strong acid (HCl; 2M)

Agitate at 40° C. for 30 minutes

Wash extract with sterile water until the pH is reverts at neutral conditions (pH 7.5)

Adjust using NaOH (0.1M) or HCL (0.2M) if necessary at room temperature.

Maintain at 4° C. overnight

Prepare a chitosan solution in 0.085% (v/v) acetic acid using and Ultra Turrax, sonicate for 30 sec to remove air pockets and maintain at 4° C. overnight.

Day 2.

Prepare a suspension of krill oil in water (1:1.5 ratio)

Homogenise using and Ultra Turrax (T25) speed 11,000 rpm for 3 minutes at 4° C. This represents the hill oil emulsion (O/W)

Pre-heat Milk Protein Concentrate (MPC) to 65° C.

Perform a two-stage hydrolysis process using a trypsin preparation with a heat-treatment step (from 3 to 10 min at 80 to 100° C.) between the two hydrolysis steps.

Cool the suspension of hydrolysed protein to 4° C. and hold for 3 hours (no agitation). This represents the hydrolysed protein suspension Prepare a 7% Maltodextrin (MD) solution (DE 16-20) with lecithin (0.03% W/v) in water Agitate at 65° C. for 30 minutes until fully hydrated Admix the hydrolysed protein solution with heated Maltodextrin to achieve an 11% solution (total solids basis).

Homogenise using an Ultrax Turrax for 1 minute at 65° C.

Add hill extract and homogenise again for using an Ultrax Turrax (T25) for 4 minute at 65° C. This represents the krill/protein/MD emulsion Mono-nuclear microcapsules were prepared using the co-extrusion laminar jet break-up technique. The encapsulator was fitted with two different sized concentric nozzles (internal and external).

krill oil/protein/MD emulsion dispersions are supplied to the internal nozzle using an air pressure regulation system which enabled flow rates of 6-10 L/min to be generated using a maximum head pressure of 0.9-1.1 bar.

The external phase (chitosan alone) is supplied using a precision syringe pump connected to the outer nozzle to flow rates of between 13 and 20 L/min.

Spherical microcapsules are obtained by the application of a set vibrational frequency, with defined amplitude, to the co-extruded liquid jet consisting of outer layer of heat-treated protein material and inner core consisting of hill oil/protein/MD emulsion The material in the inner and outer nozzle are both heated to 65° C. in order to allow for better flowability in commercial operations.

The resulting concentric jet breaks up into microcapsules, which fall into a magnetically stirred gelling bath 20 cm below the nozzle.

The gelling bath consisted of 0.3M acetic acid, 0.3 M sodium acetate, and 0.09% chitosan (high molecular weight) and 0.02% Tween-80. Temperature is maintained at 40° C.

Microcapsules are recovered after 30 minutes polymerisation in the buffer bath and washed in water Microcapsules are then vacuum dried at 40° C. to a final moisture content of 4%.

Method 5
Day 1.
Prepare 15% total solids solution using pea protein isolate (PPI)
Sonicate the solution for 3 minutes to allow full dissolution at neutral pH.
Maintain protein overnight at 4° C., pH 7.6
Take Krill oil extract and mix strong acid ($HNO_3$; 1M) with hill oil extract
Agitate at 40° C. for 30 minutes
Wash extract with sterile water until the pH is reverts at neutral conditions (pH 7.5)
Adjust using NaOH (0.1M) or HCL (0.2M) if necessary at room temperature.
Maintain at 4° C. overnight.
Prepare a chitosan solution in 1.10% (w/v) acetic acid using and Ultra Turrax, sonicate for 30 sec to remove air pockets and maintain at 4° C. overnight.
Add lecithin to the mix (0.05% w/v) and homogenise.
Prepare a separate lecithin mixture (total solids, 0.03% w/v).
Day 2.
Prepare a suspension of Krill extract in water (1:3.5 ratio)
Homogenise using and Ultra Turrax (T25) speed 11,000 rpm for 3 min at 4° C. This represents the Krill Oil emulsion (O/W)
Pre-heat PPI to 50° C.
Heat treat to 80° C. for 4 min at pH 7.6 using a microthermics/UHT unit
Cool suspension of soluble protein aggregates to 4° C. and hold for 1 hour (no agitation). This represents the heat denatured protein suspension.
Hydrate sucrose and maltodextrin i(MD) in water (based on 7.5% total solids).
Agitate at 50° C. for 30 minutes until fully hydrated
Admix the denatured PPI solution with sucrose/maltodextrin to achieve an 11% solution (total solids basis).
Agitate using an overhead paddle for 5 min at 50° C.
Add Krill oil extract and homogenise using an Ultrax Turrax (T25) for 5 minute at 50° C. This represents the Krill/protein/sucrose/MD emulsion
Mono-nuclear microcapsules were prepared using the co-extrusion laminar jet break-up technique. The encapsulator was fitted with two different sized concentric nozzles (internal and external).
Krill/protein/sucrose/MD emulsion dispersions are supplied to the internal nozzle using an air pressure regulation system which enabled flow rates of 6-10 L/min to be generated using a maximum head pressure of 0.9-1.1 bar.
The external phase (Chitosan+Lecithin, 1.10% w/v+0.03% lecithin) is supplied using a precision syringe pump connected to the outer nozzle to flow rates of between 13 and 20 L/min.
Spherical microcapsules are obtained by the application of a set vibrational frequency, with defined amplitude, to the co-extruded liquid jet consisting of outer layer of chitosan material and inner core consisting of Krill/protein/sucrose/MD emulsion.
The material in the inner and outer nozzle are both heated to 50° C. in order to allow for better flowability in commercial operations.
The resulting concentric jet breaks up into microcapsules, which fall into a magnetically stirred gelling bath 20 cm below the nozzle.
The gelling bath consisted of 0.3M acetic acid, 0.3 M sodium acetate and 0.02% lecithin. Temperature is maintained at 40° C.
Microcapsules are recovered after 15 minutes polymerisation in the buffer bath and washed in water
Microcapsules are then vacuum dried at 40° C. to a final moisture content of 4%.

Method 6
Day 1.
Prepare 13% total solids solution using whey protein isolate (WPI)
Allow protein to hydrate overnight at 4° C., pH 7.5
Take DHA/ARA and mix with strong acid (HCl; 2M)
Agitate at 40° C. for 30 minutes
Wash extract with sterile water until the pH is reverts at neutral conditions (pH 7.5)
Adjust using NaOH (0.1M) or HCL (0.2M) if necessary at room temperature.
Maintain at 4° C. overnight
Prepare a chitosan solution in 0.085% (v/v) acetic acid using and Ultra Turrax, sonicate for 30 sec to remove air pockets and maintain at 4° C. overnight.
Day 2.
Prepare a suspension of DHA/ARA in water (1:1.5 ratio)
Homogenise using and Ultra Turrax (T25) speed 11,000 rpm for 3 minutes at 4° C. This represents the DHA/ARA emulsion (O/W)
Pre-heat Whey Protein Isolate (WPI) to 65° C.
Perform a two-stage hydrolysis process using a trypsin preparation with a heat-treatment step (from 3 to 10 min at 80 to 100° C.) between the two hydrolysis steps.
Cool the suspension of hydrolysed protein to 4° C. and hold for 3 hours (no agitation). This represents the hydrolysed protein suspension
Prepare a 7% Maltodextrin (MD) solution (DE 16-20) with lecithin (0.03% W/v) in water
Agitate at 65° C. for 30 minutes until fully hydrated
Admix the hydrolysed protein solution with heated Maltodextrin to achieve an 11% solution (total solids basis).
Homogenise using an Ultrax Turrax for 1 minute at 65° C.
Add DHA/ARA extract and homogenise again for using an Ultrax Turrax (T25) for 4 minute at 65° C. This represents the DHA/ARA/protein/MD emulsion
Mono-nuclear microcapsules were prepared using the co-extrusion laminar jet break-up technique. The encapsulator was fitted with two different sized concentric nozzles (internal and external).
DHA/ARA/protein/MD emulsion dispersions are supplied to the internal nozzle using an air pressure regulation system which enabled flow rates of 6-10 L/min to be generated using a maximum head pressure of 0.9-1.1 bar.
The external phase (chitosan alone) is supplied using a precision syringe pump connected to the outer nozzle to flow rates of between 13 and 20 L/min.
Spherical microcapsules are obtained by the application of a set vibrational frequency, with defined amplitude, to the co-extruded liquid jet consisting of outer layer of heat-treated protein material and inner core consisting of DHA/ARA/protein/MD emulsion
The material in the inner and outer nozzle are both heated to 65° C. in order to allow for better flowability in commercial operations.
The resulting concentric jet breaks up into microcapsules, which fall into a magnetically stirred gelling bath 20 cm below the nozzle.

The gelling bath consisted of 0.3M acetic acid, 0.3 M sodium acetate, and 0.09% chitosan (high molecular weight) and 0.02% Tween-80. Temperature is maintained at 40° C.

Microcapsules are recovered after 30 minutes polymerisation in the buffer bath and washed in water Microcapsules are then vacuum dried at 40° C. to a final moisture content of 4%.

Method 7

Day 1.

Prepare 11% total solids solution using whey protein isolate (WPI)

Allow protein to hydrate overnight at 4° C., pH 7.5

Take Krill oil extract and mix strong acid (HCl; 2M) with krill oil extract

Agitate at 40° C. for 30 minutes

Wash hill extract with sterile water until the pH is reverts at neutral conditions (pH 7.5)

Adjust using NaOH (0.1M) or HCL (0.2M) if necessary at room temperature.

Maintain at 4° C. overnight.

Prepare a chitosan solution in 1.1% (w/v) acetic acid using and Ultra Turrax, sonicate for 30 sec to remove air pockets and maintain at 4° C. overnight.

Day 2.

Prepare a suspension of Krill extract in water (1:2 ratio)

Homogenise using and Ultra Turrax (T25) speed 11,000 rpm for 3 min at 4° C. This represents the Krill Oil emulsion (0/W)

Pre-heat WPI to 65° C.

Perform a two-stage hydrolysis process using a trypsin preparation with a heat-treatment step (from 3 to 10 min at 80 to 100° C.) between the two hydrolysis steps.

Cool the suspension of hydrolysed protein to 4° C. and hold for 3 hours (no agitation). This represents the hydrolysed protein suspension Hydrate sucrose (based on 9.2% total solids) with lecithin (0.03% W/v) in water Agitate at 65° C. for 30 minutes until fully hydrated Admix the hydrolysed protein solution with sucrose to achieve an 10.1% solution (total solids basis).

Agitate using an overhead paddle for 5 min at 65° C.

Add Krill oil extract and homogenise using an Ultrax Turrax (T25) for 4 minute at 65° C. This represents the Krill/protein/sucrose emulsion Mono-nuclear microcapsules were prepared using the co-extrusion laminar jet break-up technique. The encapsulator was fitted with two different sized concentric nozzles (internal and external).

Krill/protein/sucrose emulsion dispersions are supplied to the internal nozzle using an air pressure regulation system which enabled flow rates of 6-10 L/min to be generated using a maximum head pressure of 0.9-1.1 bar.

The external phase (Chitosan alone, 1.10% w/v) is supplied using a precision syringe pump connected to the outer nozzle to flow rates of between 13 and 20 L/min.

Spherical microcapsules are obtained by the application of a set vibrational frequency, with defined amplitude, to the co-extruded liquid jet consisting of outer layer of chitosan material and inner core consisting of Krill/protein/sucrose emulsion.

The material in the inner and outer nozzle are both heated to 65° C. in order to allow for better flowability in commercial operations.

The resulting concentric jet breaks up into microcapsules, which fall into a magnetically stirred gelling bath 20 cm below the nozzle.

The gelling bath consisted of 0.3M acetic acid, 0.3 M sodium acetate and 0.02% Tween-80. Temperature is maintained at 40° C.

Microcapsules are recovered after 15 minutes polymerisation in the buffer bath and washed in water Microcapsules are then vacuum dried at 40° C. to a final moisture content of 4%.

Method 8

Day 1.

Prepare 11% total solids solution using pea protein isolate (PPI)

Allow protein to hydrate overnight at 4° C., pH 7.5

Take Krill oil extract and mix strong acid (HCl; 2M) with krill oil extract

Agitate at 40° C. for 30 minutes

Wash hill extract with sterile water until the pH is reverts at neutral conditions (pH 7.5)

Adjust using NaOH (0.1M) or HCL (0.2M) if necessary at room temperature.

Maintain at 4° C. overnight.

Prepare a chitosan solution in 1.1% (w/v) acetic acid using and Ultra Turrax, sonicate for 30 sec to remove air pockets and maintain at 4° C. overnight.

Day 2.

Prepare a suspension of Krill extract in water (1:2 ratio)

Homogenise using and Ultra Turrax (T25) speed 11,000 rpm for 3 min at 4° C. This represents the Krill Oil emulsion (0/W)

Pre-heat PPI to 65° C.

Perform a two-stage hydrolysis process using a trypsin preparation with a heat-treatment step (from 3 to 10 min at 80 to 100° C.) between the two hydrolysis steps.

Cool the suspension of hydrolysed protein to 4° C. and hold for 3 hours (no agitation). This represents the hydrolysed protein suspension Hydrate sucrose (based on 9.2% total solids) with lecithin (0.03% W/v) in water Agitate at 65° C. for 30 minutes until fully hydrated Admix the hydrolysed protein solution with sucrose to achieve an 10.1% solution (total solids basis).

Agitate using an overhead paddle for 5 min at 65° C.

Add Krill oil extract and homogenise using an Ultrax Turrax (T25) for 4 minute at 65° C. This represents the Krill/protein/sucrose emulsion Mono-nuclear microcapsules were prepared using the co-extrusion laminar jet break-up technique. The encapsulator was fitted with two different sized concentric nozzles (internal and external).

Krill/protein/sucrose emulsion dispersions are supplied to the internal nozzle using an air pressure regulation system which enabled flow rates of 6-10 L/min to be generated using a maximum head pressure of 0.9-1.1 bar.

The external phase (Chitosan alone, 1.10% w/v) is supplied using a precision syringe pump connected to the outer nozzle to flow rates of between 13 and 20 L/min.

Spherical microcapsules are obtained by the application of a set vibrational frequency, with defined amplitude, to the co-extruded liquid jet consisting of outer layer of chitosan material and inner core consisting of Krill/protein/sucrose emulsion.

The material in the inner and outer nozzle are both heated to 65° C. in order to allow for better flowability in commercial operations.

The resulting concentric jet breaks up into microcapsules, which fall into a magnetically stirred gelling bath 20 cm below the nozzle.

The gelling bath consisted of 0.3M acetic acid, 0.3 M sodium acetate and 0.02% Tween-80. Temperature is maintained at 40° C.

Microcapsules are recovered after 15 minutes polymerisation in the buffer bath and washed in water Microcapsules are then vacuum dried at 40° C. to a final moisture content of 4%.

Invention Description

Natural encapsulation technology to ensure proper delivery and consumer satisfaction for oral delivery of lipid, especially fish oil and/or hill oil extracts. Due to the inherent emulsifying properties of krill oil, a SMEEDS mixture is prepared with ease consisting or oils, protein, carbohydrate, surfactants, and co-surfactants. Microcapsules are specifically designed for secure containment of lipids such as fish oil extracts, providing an ideal solution to address oxidation challenges often associated with marine-based omega-3 oils. This invention seeks to exploit the antioxidative properties of denatured globular proteins in the presence of carbohydrate moieties and surfactants in addition to utilizing the emulsifying properties of krill oil for the generation of stable emulsion for encapsulation purposes.

RESULTS

The oxidative stability of the oils was investigated through: (i) classical methods such as peroxide value (PV), thiobarbituric reactive substance (TBARS), and advanced methods such as determination of volatiles content by dynamic headspace (DHS)-GC/MS, lipid classes, and pyrrole content.

Oxidative Stability Degradation of encapsulated hill oil was further monitored by mid infrared (MIR) spectroscopy using attenuated total reflectance (ATR). Spectra were collected with a Tensor 27 FT-IR system (Bruker Optics, Billerica, Mass.) equipped with a Model 300 Golden Gate diamond ATR and temperature controller (Specac, Ltd., London, England). A sample was placed on the ATR crystal and heated from 25° C. to 120° C. at 5° C./min while spectra were collected at 5 minute intervals. Samples were scanned over the range 4000-600 cm-1 at a resolution of 4 cm-1. The spectrum was the result of 128 co-added scans.

FIG. 1 illustrates that Krill oil has ≤40% triglycerols (TAG) and ≤40% phospholipids compared to other marine oils (algal oils and fish oils) with >90% triglycerols. This has a significant impact upon the emulsification stability as illustrated in FIG. 2 when phospholipids from Krill oil are introduced into a protein/sucrose formulation. When the formulation is rich in phospholipids, a larger emulsion particle size and higher powder surface fat is achieved relative to triglyceride oils using the same formulation conditions i.e. protein and carbohydrate. Hence, the presence of phospholipids in krill is a significant factor to aid the generation of a stable emulsion. This is a vital factor when preparing emulsions for encapsulation processes i.e. the feed to the encapsulator must be in the form of a stable dispersion or emulsion. FIG. 3 illustrates the stability of the emulsion feed to the encapsulator using LumiFuge analysis. The narrow size distribution shows the stability of the emulsion with no evidence of phase separation. If the emulsion of Krill/protein/CHO emulsion is prepared incorrectly as outlined the invention above (i.e. incompatible ratio of protein to sucrose or maltodextrin) a very broad size distribution will be generated which cannot be extruded for encapsulation.

Figure 5:
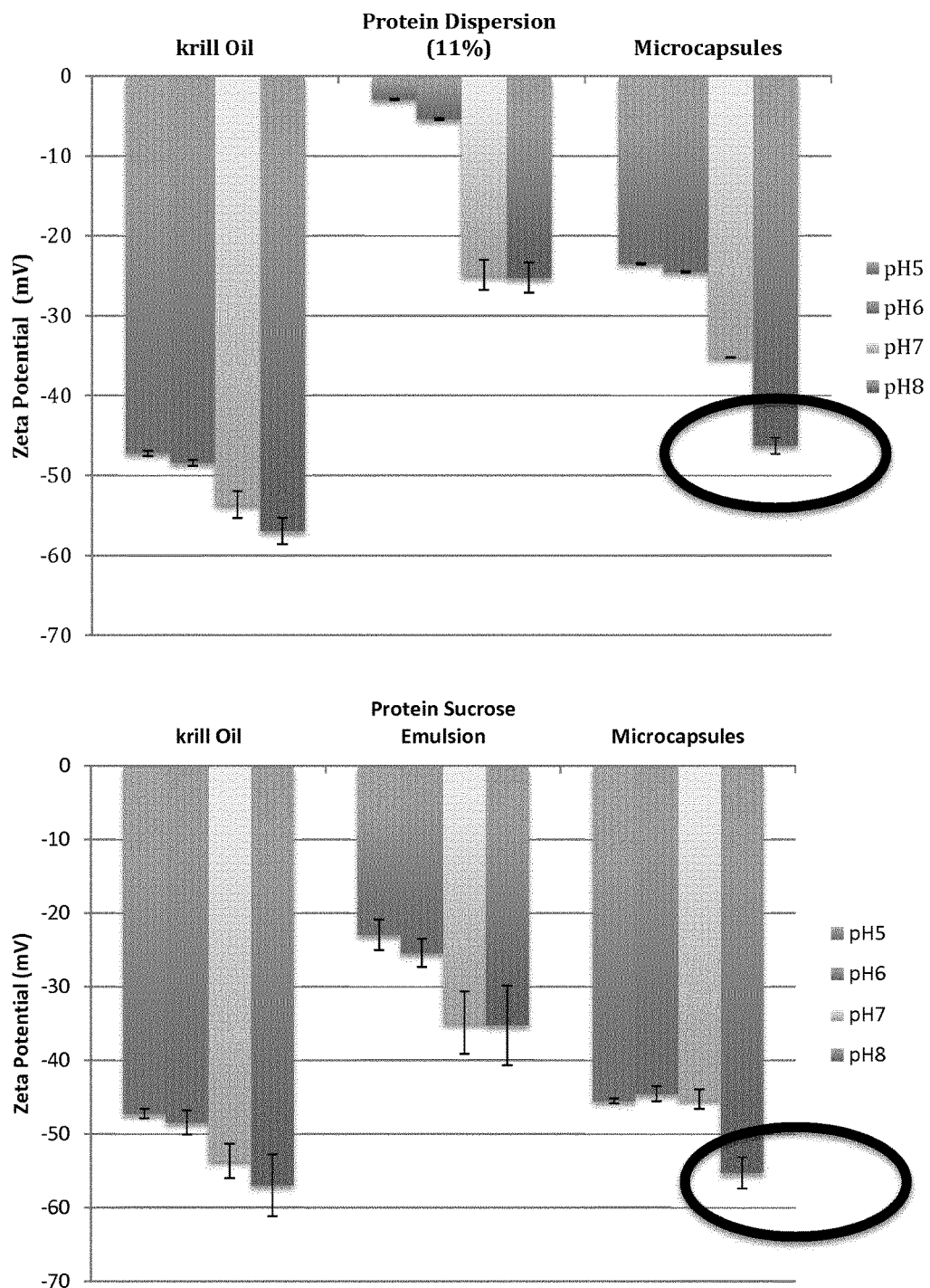
FIG. 5. Zeta Potential of different microcapsules generated using krill oil/protein emulsions vs. and hill oil/protein/sucrose/lecithin emulsions.

The compatibility of this emulsion mixture is very important for the stability and success of the encapsulation process. For this reason, zeta potential is measure in order to evaluate the compatibility of the mixture. FIG. 5 illustrates a relatively strong emulsion stability for hill oil in the microcapsule in the presence of denatured protein alone, when the pH is close to far from the isoelectric point of the protein. For pea protein or milk protein, at pH 5, the charge is almost zero (FIG. 5) since it is relatively close their respective pI values of pH4.5/pH4.8 respectively. However, when microcapsules are prepared using protein far away from the pI (i.e. pH 7/8), there is a significant increase in the charge at the oil water interface. For example, at pH 7, krill oil alone has a zeta charge of −53.62 mV±1.04 mV. Emulsions generated using denatured protein provided a relatively strong stability of approx. −46.25 mV±2.19 mV. Hence, protein as an encapsulation agent can provide significant stability for hill oil in an encapsulated form. However, in the presence of denatured protein and sucrose at a pH far from the pI, the microcapsules maintain a very stable system at the oil water interface with a zeta potential of −55.26 mV±5.31 mV. Hence, it is clear that denature protein can provide a stable emulsion for encapsulation; however the addition of sucrose and further enhance this stabilization effect.

Figure 6:
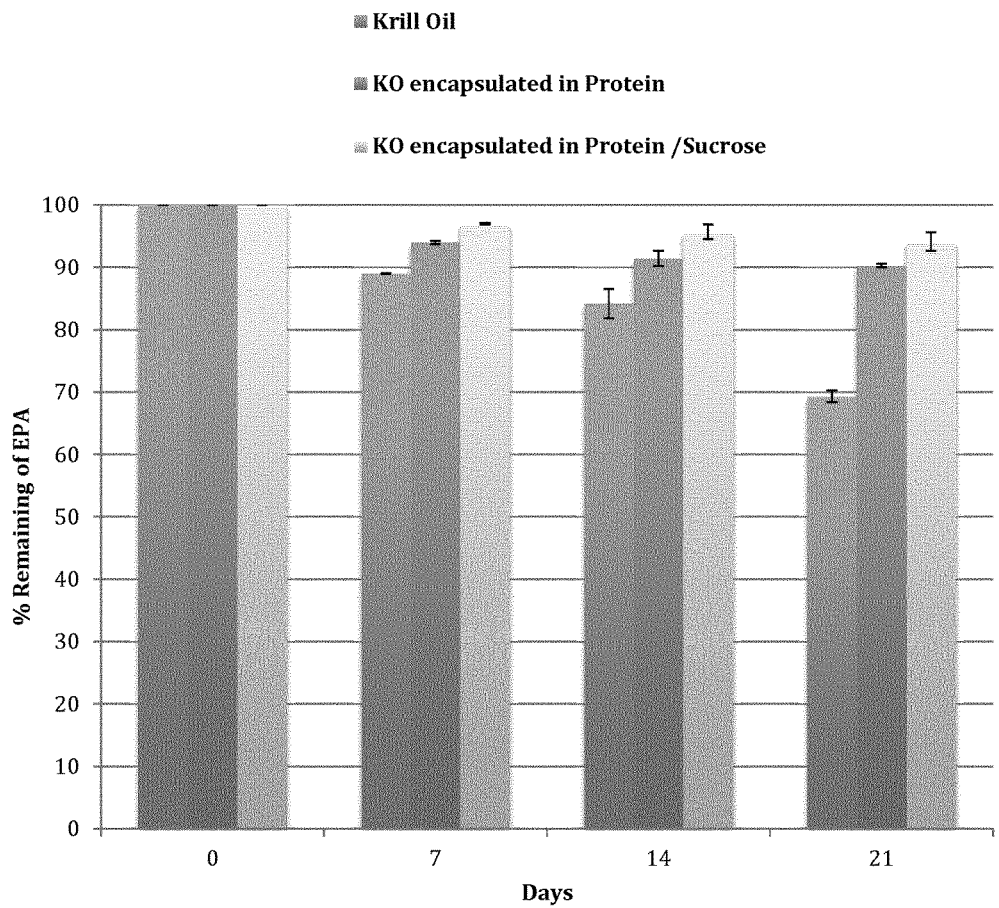
FIG. 6. EPA stability during accelerated storage of hill micro-capsules with lecithin at 40 Deg C. for 21 days.
Figure 7:
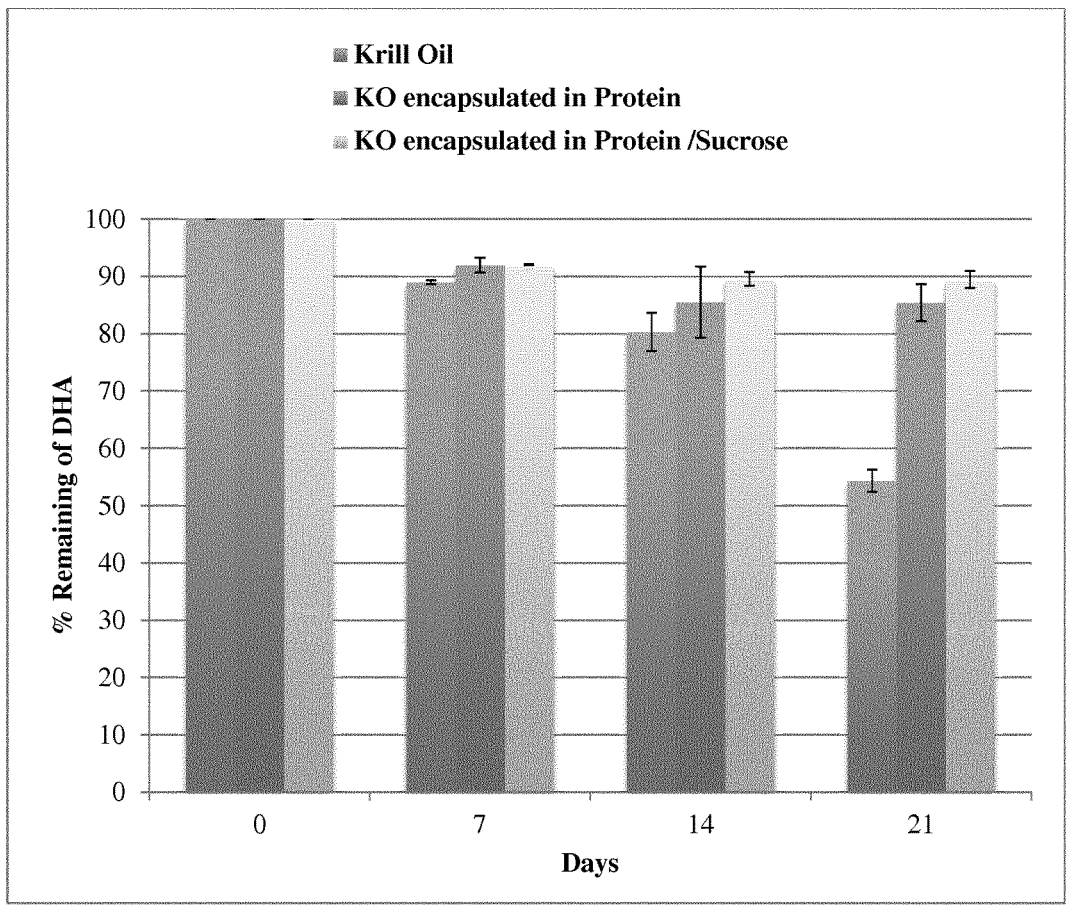
FIG. 7. DHA stability during accelerated storage of hill micro-capsules with lecithin at 40 Deg C. for 21 days.
Figure 8:
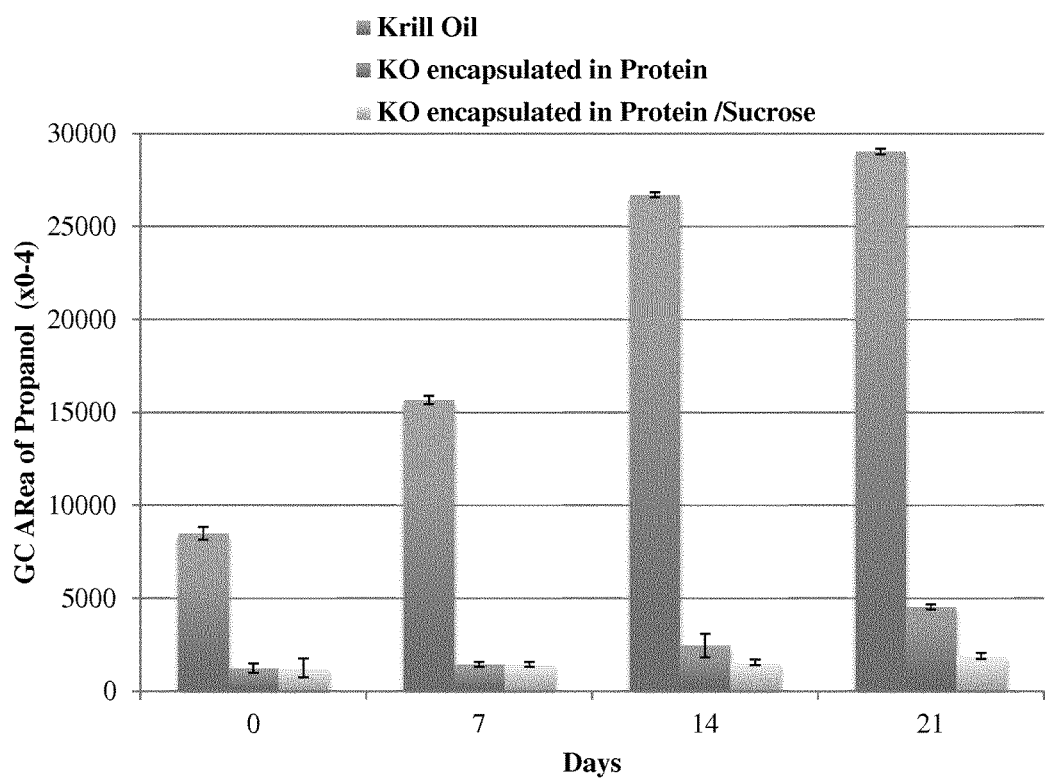
FIG. 8 Overall stability during accelerated storage of krill micro-capsules with lecithin at 40 Deg C. for 21 days.

FIGS. 6, 7 and 8 illustrate the stability of microcapsules during storage at 40° C. for 21 days. Data to date illustrates that encapsulation enhances DHA and ARA stability by 35.74% and 64.47%, respectively. It is clear that the encapsulation of denatured protein and sucrose in the presence of lecithin provides a significant stabilization factor. Hence, encapsulation significantly improved the storage stability of hill oil and heat treated protein+sucrose+lecithin microcapsules provided the best protection against oxidation (FIG. 8).

FIG. 8 shows a reduced production of volatile oxidation products (93.42%), as a result of encapsulation, which demonstrates improved product palatability. This encapsulation processes demonstrated significant improvements in krill oil stability and significantly reduced oxidation products. This novel technology and provides market opportunities for emerging krill oil applications.

Figure 9:
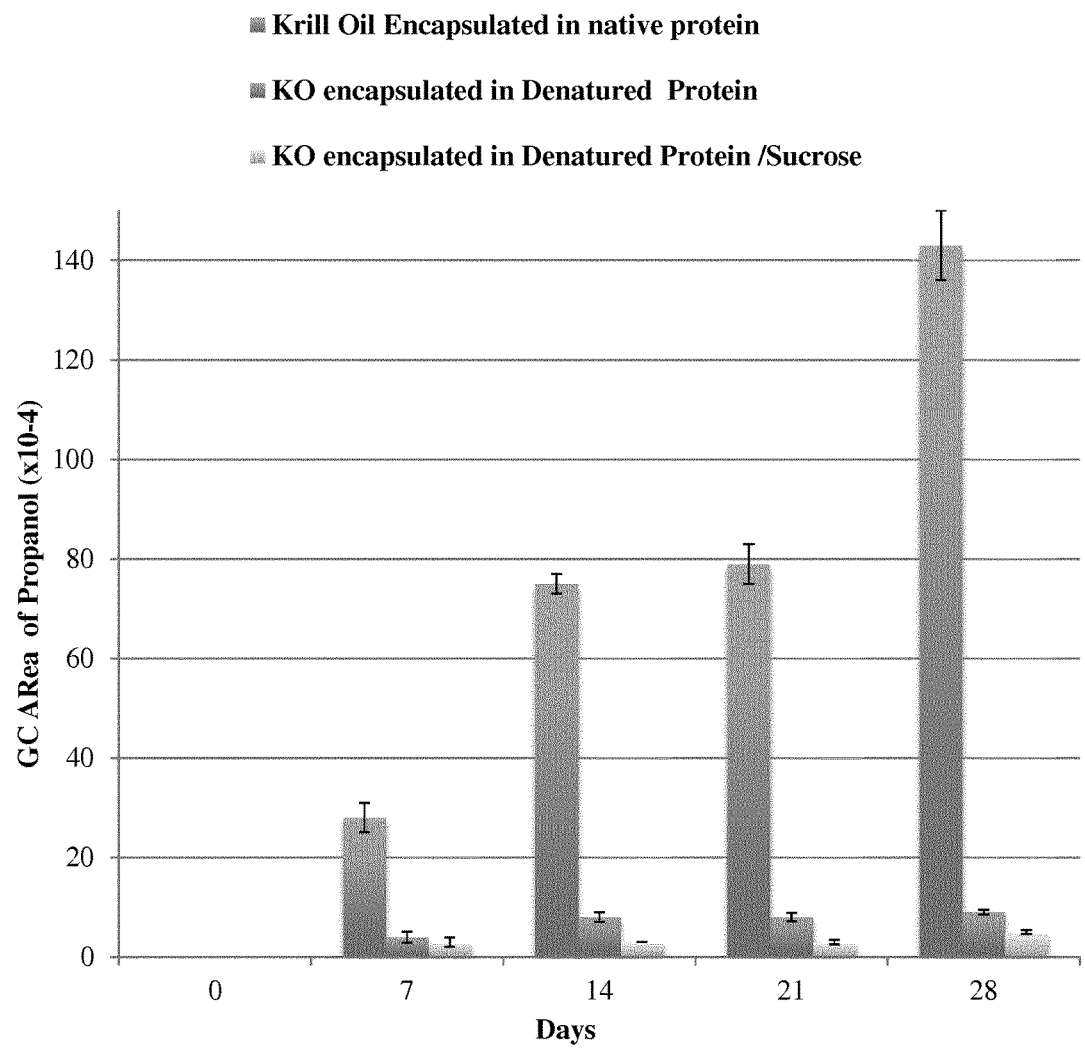
FIG. 9. Overall stability during accelerated storage of vacuum dried hill micro-capsules with lecithin at 40 Deg C. for 21 days.
Figure 10:
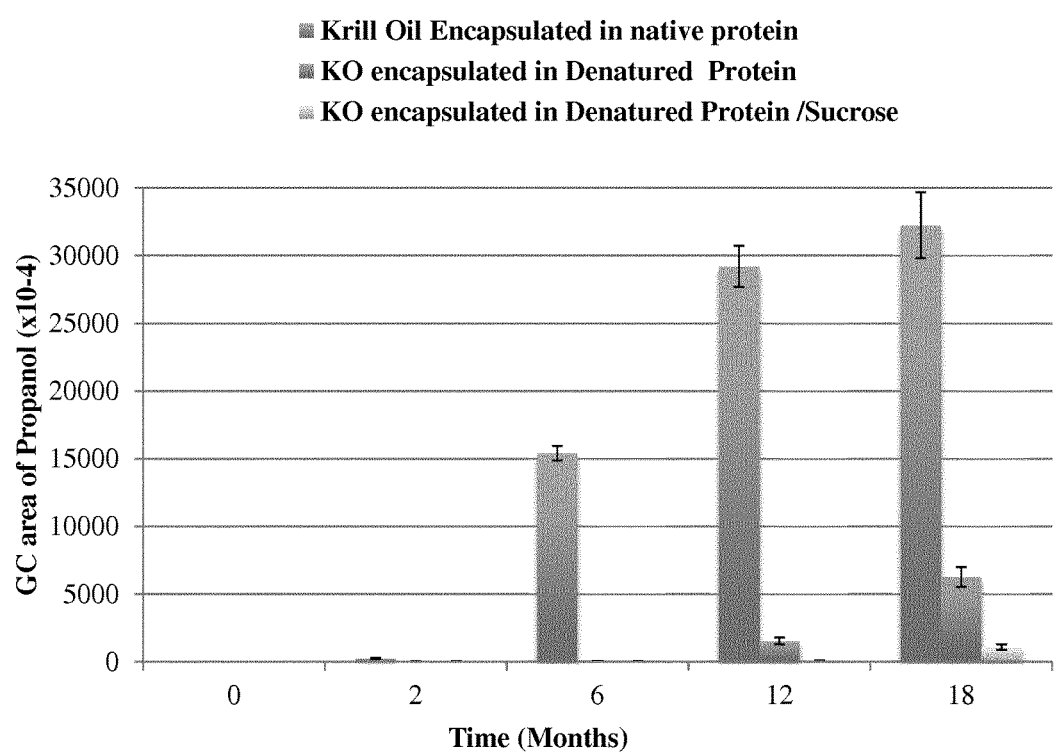
FIG. 10. Overall stability of microcapsules with lecithin in a powdered format during storage at 20° C. for 18 months.
Figure 11:
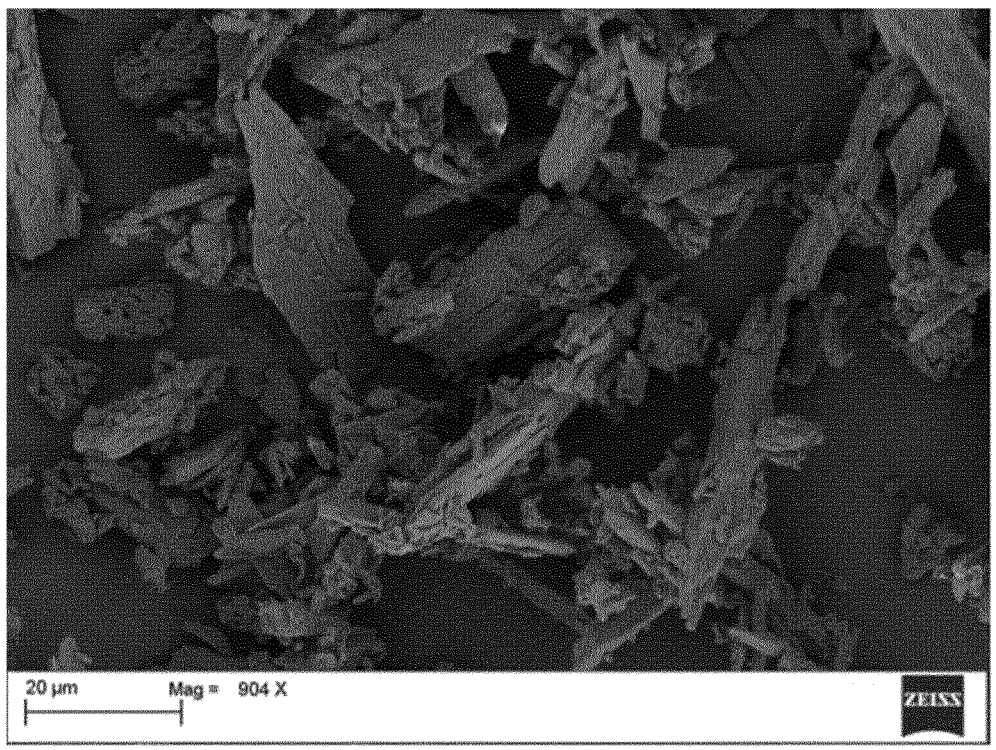
FIG. 11. SEM image of krill oil encapsulated the presence of native protein and sucrose mixture.
Figure 12:
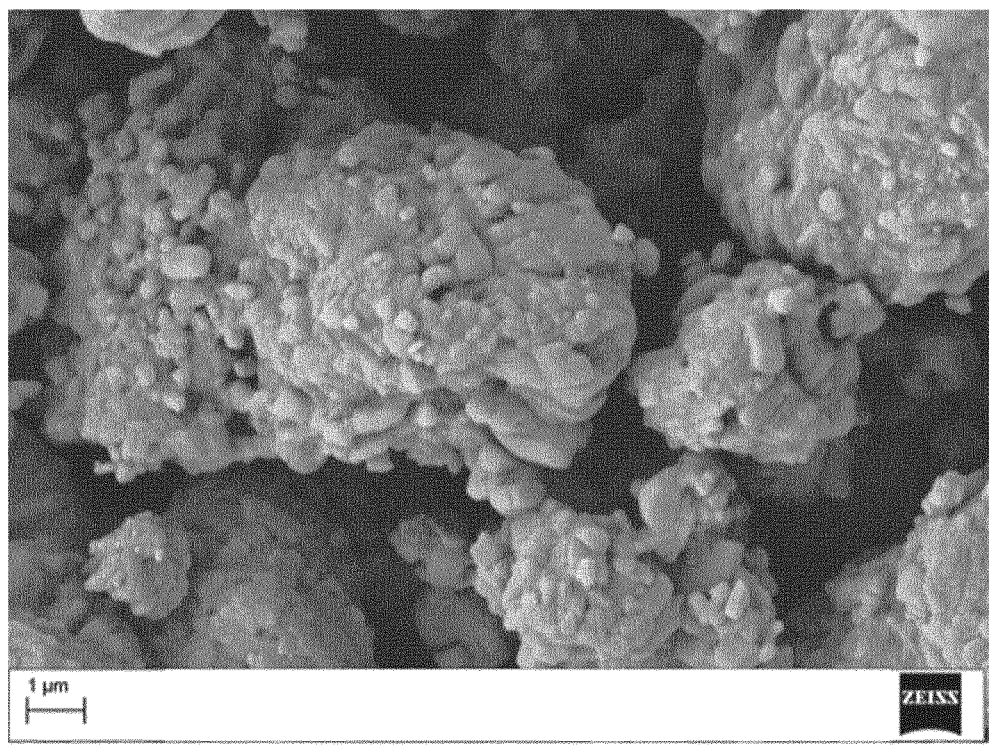
FIG. 12. SEM image of hill oil encapsulated the presence of denatured WPI protein, sucrose, lecithin and chitosan mixture.
Figure 13:
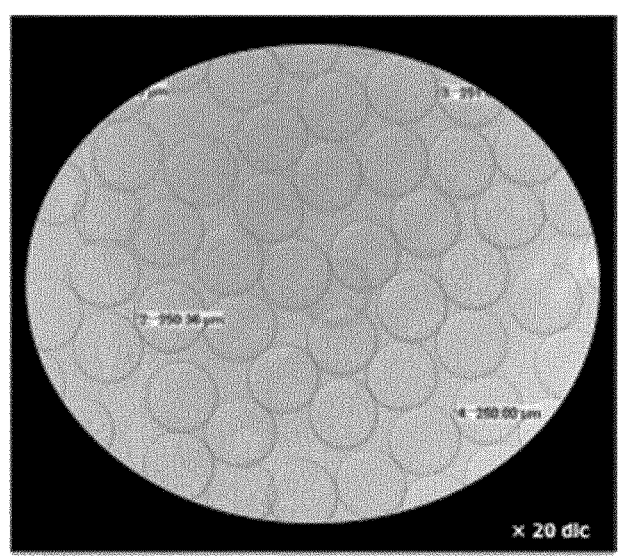
FIG. 13. Light Microscope image of krill oil encapsulated the presence of denatured WPI protein, sucrose, lecithin and chitosan mixture.

After vacuum drying the microcapsules had moisture content of 4% and they were subsequently stored at room temperature for 21 days in the powdered form. FIG. 9 illustrates the significant difference in oxidative protection provided by native protein in comparison to denatured protein emulsified and encapsulated with sucrose and lecithin. This SMEEDS mixture clearly exemplifies a mechanism of protection for fatty acid mixtures such as hill oil. FIG. 10 further extended the storage of these powders and endorsed the long-term stability of encapsulated hill oil via co-extrusion and encapsulation of a SMEEDS mixture. Encapsulation enhanced the oxidative stability of the hill oily 96.62%±0.34% relative to free krill oil suspensions. Hence the formulation as per the SMEEDS strategy provide for a stable and palatable product.

The invention claimed is:

1. A gelated mono-nuclear microencapsulate, formed by extrusion of microdroplets into an acidic gelling bath for immediate curing therein, comprising a lipid microemulsion core encapsulated within a gastro-resistant and ileal sensitive polymerized chitosan membrane shell, wherein the lipid microemulsion core includes a denatured or hydrolysed protein, a carbohydrate, and a lipid in a microemulsion that is a self microemulsifying drug delivery system containing a surfactant and a co-surfactant; and the shell is impermeable to air.

2. A gelated mono-nuclear microencapsulate as claimed in claim 1 in which the lipid is selected from a marine-derived lipid; a lipid derived from nuts, seeds, or eggs; a fatty acid; and a triglyceride.

3. A gelated mono-nuclear microencapsulate as claimed in claim 1 in which the lipid is a marine derived oil selected from fish oil, hill oil, and algal oil.

4. A gelated mono-nuclear microencapsulate as claimed in claim 1 in which the lipid is a fatty acid selected from docosahexaenoic acid (DHA) and arachidonic acid (ARA).

5. A gelated mono-nuclear microencapsulate as claimed in claim 1 in which the carbohydrate is a polysaccharide.

6. A gelated mono-nuclear microencapsulate as claimed in claim 1 in which the carbohydrate is a glucose-containing polysaccharide, optionally selected from maltodextrin, sucrose, and maltose.

7. A gelated mono-nuclear microencapsulate as claimed in claim 1 in which the carbohydrate is a disaccharide.

8. A gelated mono-nuclear microencapsulate as claimed in claim 1 in which the carbohydrate has a dextrose equivalence of 16-20.

9. A gelated mono-nuclear microencapsulate as claimed in claim 1 in which the shell further includes a co-surfactant that, optionally, is lecithin.

10. A gelated mono-nuclear microencapsulate as claimed in claim 1 in which the shell further includes a denatured or hydrolysed protein.

11. A gelated mono-nuclear microencapsulate as claimed in claim 1 in which the denatured or hydrolysed protein of the lipid microemulsion core comprises a dairy protein, a vegetable protein, or both.

12. A gelated mono-nuclear microencapsulate as claimed in claim 1 in which:
the lipid microemulsion core comprises 5.5 to 86.0% total solids (w/v); and/or
the lipid microemulsion core comprises 5.5 to 15% denatured or hydrolysed protein (w/v); and/or
the lipid microemulsion core comprises 2.0 to 8.5% carbohydrate (w/v).

13. A gelated mono-nuclear microencapsulate as claimed in claim 1 in which the microencapsulate is dried.

14. A composition suitable for oral administration to a mammal, the composition comprising a multiplicity of microencapsulates according to claim 1.

15. A composition suitable for oral administration to a mammal, the composition comprising a multiplicity of microencapsulates according to claim 1, wherein the composition is selected from a food product, a beverage, a food ingredient, an animal feed ingredient, a nutritional supplement, an infant formula, an animal feed supplement, and an oral dosage pharmaceutical.

16. A composition suitable for oral administration to a mammal, the composition comprising a multiplicity of microencapsulates according to claim 1, wherein the composition is an infant formula and the lipid in each of the microencapsulates is selected from DHA and ARA.

* * * * *